US012611139B2

(12) United States Patent
Gill et al.

(10) Patent No.: US 12,611,139 B2
(45) Date of Patent: Apr. 28, 2026

(54) METHODS, SYSTEMS, AND DEVICES FOR DETECTING SLEEP AND APNEA EVENTS

(71) Applicant: Pacesetter, Inc., Sylmar, CA (US)

(72) Inventors: Jong Gill, Valencia, CA (US); Prakrit Shrestha, Los Angeles, CA (US); Kyungmoo Ryu, Palmdale, CA (US)

(73) Assignee: Pacesetter, Inc., Sylmar, CA (US)

( * ) Notice: Subject to any disclaimer, the term of this patent is extended or adjusted under 35 U.S.C. 154(b) by 14 days.

(21) Appl. No.: 18/509,162

(22) Filed: Nov. 14, 2023

(65) Prior Publication Data

US 2024/0081734 A1      Mar. 14, 2024

Related U.S. Application Data

(63) Continuation of application No. 17/235,807, filed on Apr. 20, 2021, now Pat. No. 11,896,387.
(Continued)

(51) Int. Cl.
  *A61B 5/00* (2006.01)
  *A61B 5/0205* (2006.01)
  (Continued)

(52) U.S. Cl.
  CPC .......... *A61B 5/4818* (2013.01); *A61B 5/0205* (2013.01); *A61B 5/1116* (2013.01);
  (Continued)

(58) Field of Classification Search
  CPC .............................. A61B 5/4818; A61B 5/349
  (Continued)

(56) References Cited

U.S. PATENT DOCUMENTS

| | | |
|---|---|---|
| 7,189,204 B2 | 3/2007 | Ni et al. |
| 7,343,198 B2 | 3/2008 | Behbehani et al. |

(Continued)

FOREIGN PATENT DOCUMENTS

| | | | |
|---|---|---|---|
| CN | 1897872 A | | 1/2007 |
| CN | 107967684 A | * | 4/2018 |

(Continued)

OTHER PUBLICATIONS

Response to Office Action dated Nov. 6, 2024, Chinese Patent Application No. 202110599255.4.

(Continued)

*Primary Examiner* — Nicole F Johnson
(74) *Attorney, Agent, or Firm* — Pearl Cohen Zedek Latzer Baratz LLP

(57) ABSTRACT

Described herein are apparatuses and methods for classifying a patient as being asleep or awake. Such an apparatus can include an accelerometer and a processor. The accelerometer, alone or in combination with the processor, is used to determine an activity level of the patient and a posture of the patient. The processor is configured to classify the patient as being asleep in response to both (i) the posture of the patient being recumbent or reclined for at least a sleep latency duration, and (ii) the activity level of the patient not exceeding an activity threshold for at least the sleep latency duration; and classify the patient as being awake in response to at least one of (iii) the posture of the patient being upright for at least an awake latency duration, or (iv) the activity level of the patient exceeding the activity threshold for at least the awake latency duration.

28 Claims, 16 Drawing Sheets

Related U.S. Application Data

(60) Provisional application No. 63/088,947, filed on Oct. 7, 2020, provisional application No. 63/052,877, filed on Jul. 16, 2020, provisional application No. 63/033,553, filed on Jun. 2, 2020.

(51) Int. Cl.

| | |
|---|---|
| *A61B 5/11* | (2006.01) |
| *A61B 5/349* | (2021.01) |
| *A61B 5/366* | (2021.01) |
| *G16H 40/67* | (2018.01) |
| *A61B 5/024* | (2006.01) |
| *A61B 5/352* | (2021.01) |
| *A61B 5/353* | (2021.01) |
| *A61B 5/355* | (2021.01) |
| *A61B 5/358* | (2021.01) |
| *A61B 5/36* | (2021.01) |

(52) U.S. Cl.
CPC ............ *A61B 5/1118* (2013.01); *A61B 5/349* (2021.01); *A61B 5/366* (2021.01); *A61B 5/686* (2013.01); *A61B 5/7221* (2013.01); *G16H 40/67* (2018.01); *A61B 5/02405* (2013.01); *A61B 5/352* (2021.01); *A61B 5/353* (2021.01); *A61B 5/355* (2021.01); *A61B 5/358* (2021.01); *A61B 5/36* (2021.01); *A61B 2562/0219* (2013.01)

(58) Field of Classification Search
USPC ......................................................... 600/301
See application file for complete search history.

(56) References Cited

U.S. PATENT DOCUMENTS

| | | | |
|---|---|---|---|
| 7,404,799 B1 | 7/2008 | Koh | |
| 7,438,686 B2 | 10/2008 | Cho et al. | |
| 7,467,012 B1 | 12/2008 | Park et al. | |
| 7,491,181 B2 | 2/2009 | Heruth et al. | |
| 7,725,181 B1 | 5/2010 | Bornzin et al. | |
| 7,738,936 B1 | 6/2010 | Turcott | |
| 7,775,993 B2 | 8/2010 | Heruth et al. | |
| 7,787,946 B2 | 8/2010 | Stahmann et al. | |
| 7,801,593 B2 | 9/2010 | Behbehani et al. | |
| 7,909,771 B2 | 3/2011 | Meyer et al. | |
| 7,942,822 B1 | 5/2011 | Koh | |
| 8,083,682 B2 | 12/2011 | Dalai et al. | |
| 8,262,578 B1 | 9/2012 | Bharmi et al. | |
| 8,337,431 B2 | 12/2012 | Heruth et al. | |
| 8,535,222 B2 | 9/2013 | Ni et al. | |
| 8,679,024 B2 | 3/2014 | Zhang et al. | |
| 8,758,242 B2 | 6/2014 | Miesel et al. | |
| 8,781,587 B2 | 7/2014 | Alt et al. | |
| 8,956,295 B2 | 2/2015 | Ni et al. | |
| 9,174,055 B2 * | 11/2015 | Davis ..................... | G16H 15/00 |
| 9,333,351 B2 | 5/2016 | Arnold et al. | |
| 10,765,359 B2 | 9/2020 | Cho et al. | |
| 2003/0153955 A1 | 8/2003 | Park et al. | |
| 2005/0148897 A1 | 7/2005 | Cho et al. | |
| 2005/0245988 A1 * | 11/2005 | Miesel ................. | A61B 5/0205 607/46 |
| 2007/0032733 A1 | 2/2007 | Burton | |
| 2007/0156059 A1 | 7/2007 | Vitali et al. | |
| 2007/0167851 A1 | 7/2007 | Luca et al. | |
| 2012/0123232 A1 | 5/2012 | Najarian | |
| 2015/0164410 A1 | 6/2015 | Selvaraj et al. | |
| 2017/0347969 A1 | 12/2017 | Thakur | |
| 2018/0021010 A1 | 1/2018 | Stamatopoulos et al. | |
| 2019/0053754 A1 | 2/2019 | Gowda et al. | |
| 2021/0369191 A1 | 12/2021 | Gill et al. | |

FOREIGN PATENT DOCUMENTS

| | | | | | |
|---|---|---|---|---|---|
| EP | 157425 | B1 | 2/2008 | | |
| EP | 1732442 | B1 | 11/2009 | | |
| EP | 1732436 | B1 | 4/2010 | | |
| EP | 1711104 | B1 | 3/2014 | | |
| EP | 2395911 | B1 | 6/2020 | | |
| WO | WO-2005089863 | A1 * | 9/2005 | ........ | A61M 5/14276 |
| WO | WO-2017184753 | A1 * | 10/2017 | .......... | A61N 1/3601 |
| WO | WO-2017217597 | A1 * | 12/2017 | .......... | A61B 5/0006 |

OTHER PUBLICATIONS

English translation of Specification and Claim Amendments filed in Response to Office Action dated Nov. 6, 2024, Chinese Patent Application No. 202110599255.4.

Office Action dated Apr. 10, 2024, Chinese Patent Application No. 202110599255.4.

Response to Office Action dated Feb. 29, 2024, Chinese Patent Application No. 202110599255.4.

Office Action dated Aug. 8, 2024, Chinese Patent Application No. 202110599255.4.

Office Action dated Sep. 6, 2024, European Patent Application No. 21170341.8-1113.

English Abstract of Chinese Publication No. CN1897872 published Jan. 17, 2007.

Response to Office Action dated Nov. 9, 2024, European Patent Application No. 21170341.8.

Response to Office Action dated Jun. 11, 2024, Chinese Patent Application No. 202110599255.4.

Rahmand, MD Juber, et al., "Severity classification of obstructive sleep apnea using only heard rate variability measures with an ensemble classifier," 2018 IEEE EMBS International Conference on Biomedical & Health Informatics, Mar. 4, 2018, pp. 33-36.

Czopek, Klaudia, "Significance of snoring and other sounds appearing during the night based on the ECG," Computing in Cardiology, Sep. 9, 2012, pp. 637-640.

Extended European Search Report dated Nov. 11, 2021, European Patent Application No. 21170341.8-1113.

Response to Extended European Search Report dated Dec. 20, 2021, European Patent Application No. 21170341.8-1113.

Restriction Requirement dated Feb. 16, 2023, U.S. Appl. No. 17/235,807, filed Apr. 20, 2021.

Response to Restriction dated Feb. 22, 2023, U.S. Appl. No. 17/235,807, filed Apr. 20, 2021.

Non-final Office Action dated Apr. 25, 2023, U.S. Appl. No. 17/235,807, filed Apr. 20, 2021.

Response to Office Action dated May 25, 2023, U.S. Appl. No. 17/235,807, filed Apr. 20, 2021.

Final Office Action dated Aug. 23, 2023, U.S. Appl. No. 17/235,807, filed Apr. 20, 2021.

Response to Office Action dated Oct. 6, 2023, U.S. Appl. No. 17/235,807, filed Apr. 20, 2021.

Notice of Allowance dated Oct. 25, 2023, U.S. Appl. No. 17/235,807, filed Apr. 20, 2021.

Chinese Office Action dated Nov. 10, 2023, Chinese Patent Application No. 202110599255.4.

U.S. Appl. No. 18/535,654, filed Dec. 11, 2023.

Communication pursuant to Article 94(3) EPC dated Jun. 17, 2025, European Patent Application No. 21170341.8-1113.

Response to Communication pursuant to Article 94(3) EPC dated Jul. 10, 2025, European Patent Application No. 21170341.8-1113.

Non-final Office Action dated Jul. 28, 2025, U.S. Appl. No. 18/535,654, filed Dec. 11, 2023.

Response to Office Action dated Aug. 6, 2025, U.S. Appl. No. 18/535,654, filed Dec. 11, 2023.

Non-final Office Action dated Oct. 17, 2025, U.S. Appl. No. 18/535,654, filed Dec. 11, 2023.

Response to Office Action dated Oct. 23, 2025, U.S. Appl. No. 18/535,654, filed Dec. 11, 2023.

Final Office Action dated Jan. 15, 2026, U.S. Appl. No. 18/535,654, filed Dec. 11, 2023.

(56) References Cited

OTHER PUBLICATIONS

Response to Office Action dated Jan. 29, 2026, U.S. Appl. No.
18/535,654, filed Dec. 11, 2023.

* cited by examiner

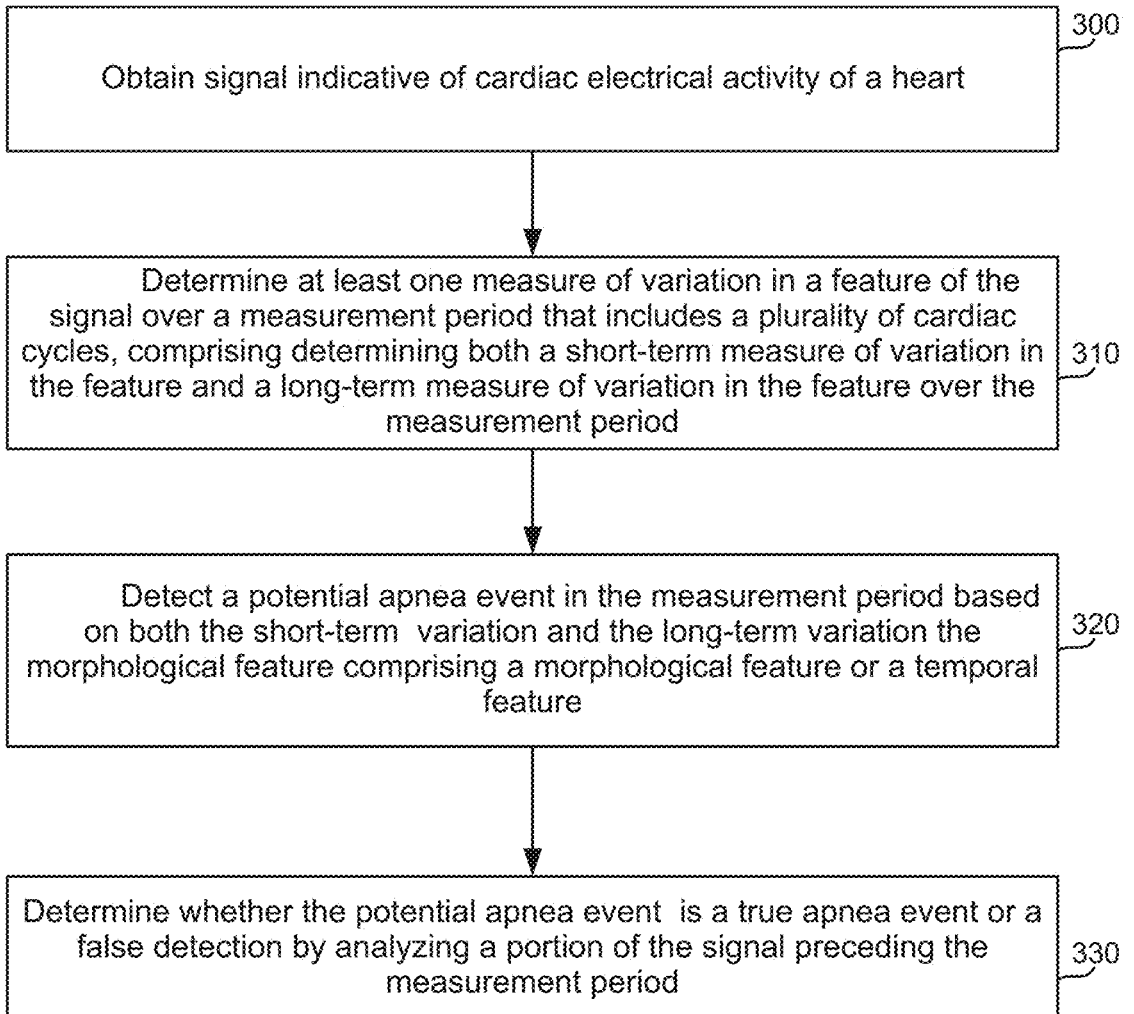

Obtain signal indicative of cardiac electrical activity of a heart

300

Determine at least one measure of variation in a feature of the signal over a measurement period that includes a plurality of cardiac cycles, comprising determining both a short-term measure of variation in the feature and a long-term measure of variation in the feature over the measurement period

310

Detect a potential apnea event in the measurement period based on both the short-term variation and the long-term variation the morphological feature comprising a morphological feature or a temporal feature

320

Determine whether the potential apnea event is a true apnea event or a false detection by analyzing a portion of the signal preceding the measurement period

Determine a short term variation in the at least one feature — 400

Compare the STV over the measurement period to a threshold STV — 450

Is STV < threshold for at least specified duration? — 460

NO

YES

Potential apnea event detected — 440

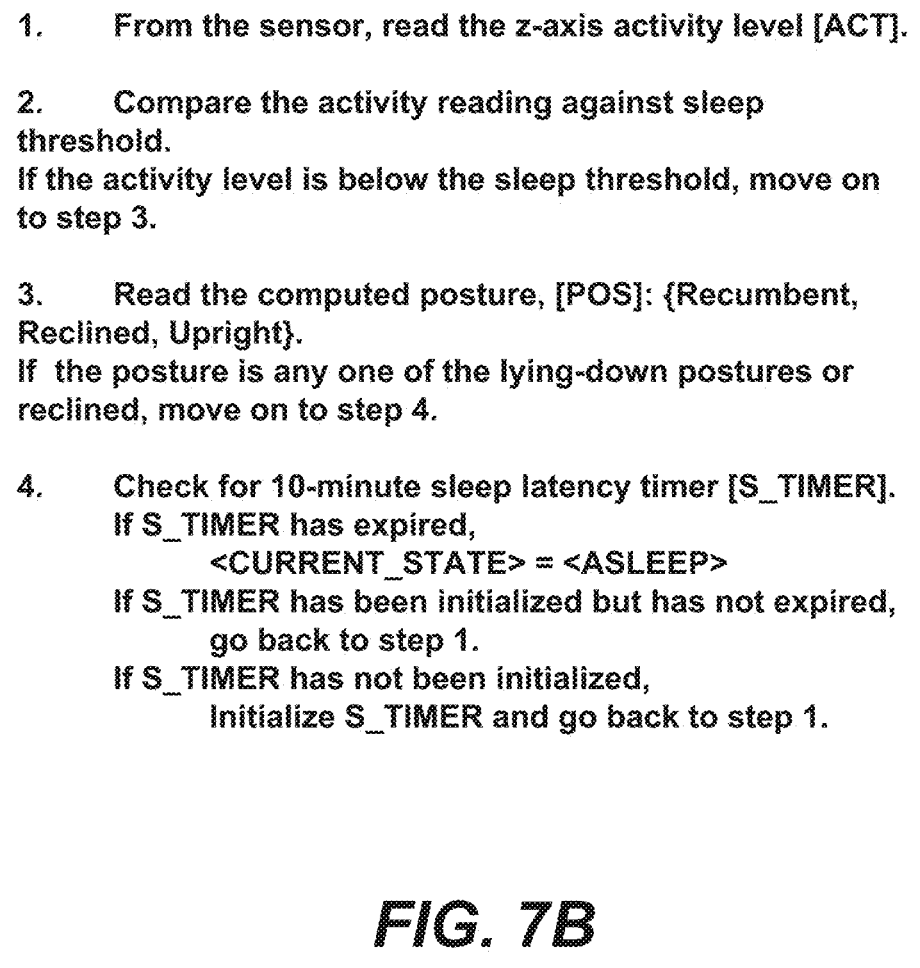

1.      From the sensor, read the z-axis activity level [ACT].

2.      Compare the activity reading against sleep threshold.
If the activity level is below the sleep threshold, move on to step 3.

3.      Read the computed posture, [POS]: {Recumbent, Reclined, Upright}.
If  the posture is any one of the lying-down postures or reclined, move on to step 4.

4.      Check for 10-minute sleep latency timer [S_TIMER].
        If S_TIMER has expired,
              <CURRENT_STATE> = <ASLEEP>
        If S_TIMER has been initialized but has not expired,
              go back to step 1.
        If S_TIMER has not been initialized,
              Initialize S_TIMER and go back to step 1.

FIG. 7B

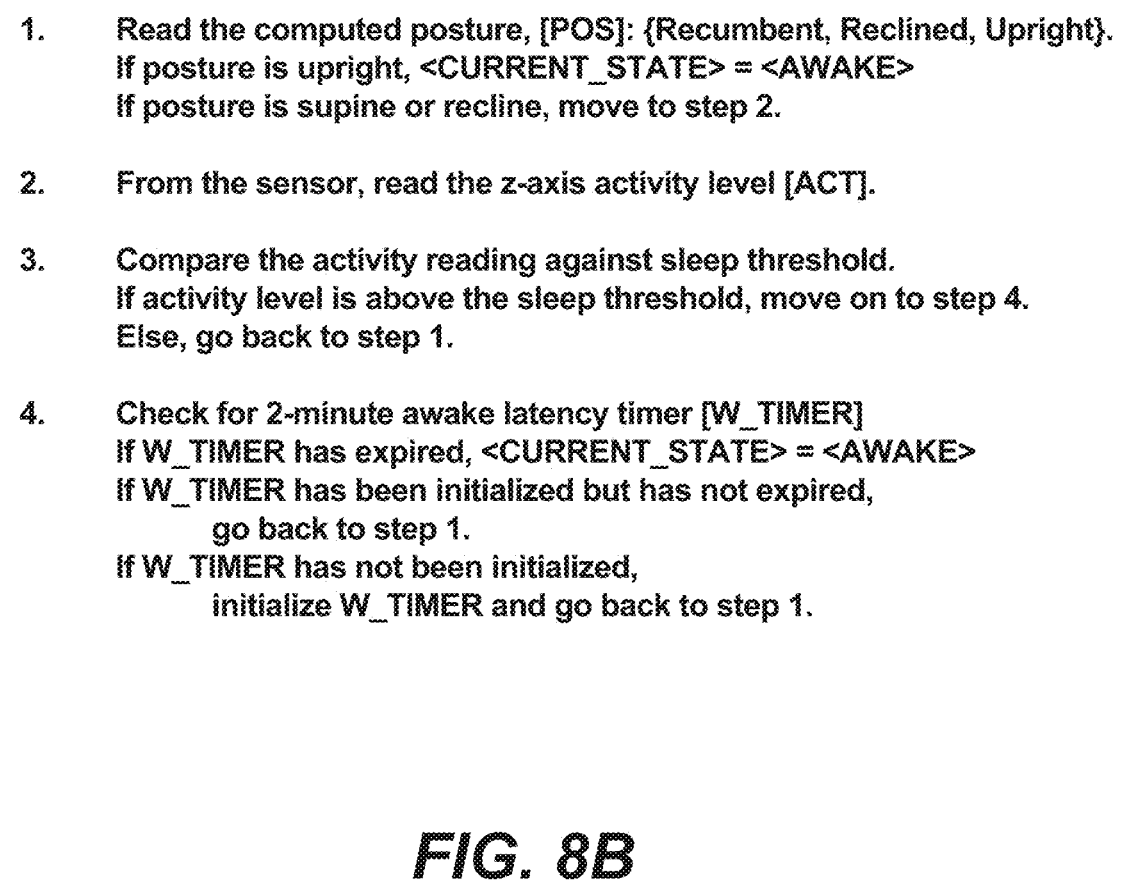

1.    Read the computed posture, [POS]: {Recumbent, Reclined, Upright}.
      If posture is upright, <CURRENT_STATE> = <AWAKE>
      If posture is supine or recline, move to step 2.

2.    From the sensor, read the z-axis activity level [ACT].

3.    Compare the activity reading against sleep threshold.
      If activity level is above the sleep threshold, move on to step 4.
      Else, go back to step 1.

4.    Check for 2-minute awake latency timer [W_TIMER]
      If W_TIMER has expired, <CURRENT_STATE> = <AWAKE>
      If W_TIMER has been initialized but has not expired,
            go back to step 1.
      If W_TIMER has not been initialized,
            initialize W_TIMER and go back to step 1.

FIG. 8B

METHODS, SYSTEMS, AND DEVICES FOR DETECTING SLEEP AND APNEA EVENTS

PRIORITY CLAIM

The present application is a continuation of U.S. patent application Ser. No. 17/235,807, titled "METHODS, SYSTEMS, AND DEVICES FOR DETECTING SLEEP AND APNEA EVENTS," which was filed Apr. 20, 2021, issued as U.S. Pat. No. 11,896,387, on Feb. 13, 2024, which claims priority to each of the following applications: U.S. Provisional Patent Application No. 63/088,947, titled METHODS, SYSTEMS, AND DEVICES FOR DETECTING SLEEP AND APNEA EVENTS, which was filed on Oct. 7, 2020; U.S. Provisional Patent Application No. 63/052,877, titled DETECTING APNEA EVENTS USING A CARDIAC SIGNAL, which was filed on Jul. 16, 2020; and U.S. Provisional Patent Application No. 63/033,553, titled DETECTING APNEA EVENTS USING A CARDIAC SIGNAL, which was filed on Jun. 2, 2020. Each of the above applications is incorporated by reference herein.

FIELD OF TECHNOLOGY

Embodiments described herein generally relate to methods, systems, and devices (aka apparatuses) for detecting apnea events in human patients, and more particularly, for detecting apnea events using cardiac rhythms. Embodiments described also relate to methods, systems, and devices for detecting when a patient is awake, and when a patient is asleep, which information can be used to selectively enable and disable monitoring for sleep apnea events, and/or in other manners.

BACKGROUND

Sleep apnea syndrome (SAS) is a breathing disorder characterized by repeated episodes of reduced (hypopnea) or absent (apnea) airflow. SAS is common in middle-aged women and men and can lead myriad maladies adversely affecting one's quality of life. It can be present with other cardiovascular comorbidities such as arrhythmia, coronary artery disease, and heart failure. One method of diagnosing SAS is sleep study via overnight polysomnography (PSG). However, this method is costly, uncomfortable for the patient and requires extended evaluation time.

Various types of devices can provide cardiogram data normally used for diagnosing cardiac issues. Such devices include surface (skin) mounted medical devices and implantable medical devices (IMDs). Some types of IMDs, such as implantable cardiac pacemakers and implantable cardiac defibrillators (ICDs), are capable of providing not only data, but treatment of cardiac issues. Other types of IMDs, such as insertable cardiac monitors (ICMs), are used for diagnostic purposes.

Techniques have been developed using implantable devices to use impedance-based techniques to detect SAS and provide long-term information on changes in the severity of SAS over time. Impedance based detectors require a dedicated impedance module for SAS assessment, which may not be readily available in all IMDs. Intracardiac electrogram (IEGM) is readily available in almost all ICDs. Computationally based IMD SAS monitoring was developed using a frequency domain-based, Fast Fourier Transfer algorithm. However, this algorithm is computationally intensive, which can require significant current drain from the battery powering an IMD device.

SAS only occurs while a person is asleep. Accordingly, when monitoring for SAS, it is helpful to know whether a person is asleep or awake.

SUMMARY

Certain embodiments of the present technology are directed to apparatuses, methods, and non-transitory computer readable medium storing instructions that can be used to detect an apnea event. Such an apparatus can comprise sensing circuitry couplable to electrodes and configured to sense a signal indicative of cardiac electrical activity of a patient's heart. The apparatus can also include at least one processor configured to determine a measure of short-term variation (STV) and a measure of long-term variation (LTV) in a feature of the signal over a measurement period that includes a plurality of cardiac cycles, and detect a potential apnea event in the measurement period based on the measure of STV and the measure of LTV in the feature; wherein the feature comprises one of a morphological feature or a temporal feature. In accordance with certain embodiments, the apparatus comprises one of an implantable pacemaker, an implantable cardiac defibrillator, an implantable cardiac monitor, or a non-implanted apparatus.

In accordance with certain embodiments, the at least one processor of the apparatus is configured to detect the potential apnea event by determining that the measure of LTV is greater than the measure of STV for at least the measurement period. In accordance with other embodiments, the at least one processor of the apparatus is configured to detect the potential apnea event by determining that the measure of LTV is greater than the measure of STV for at least the measurement period, and the measure of STV is less that a specified threshold for at least the measurement period.

In accordance with certain embodiments, the at least one processor of the apparatus is configured to: identify individual cardiac cycles within the signal indicative of cardiac electrical activity of a patient's heart; determine the measure of SW based on a first number of the individual cardiac cycles; and determine the measure of LTV based on a second number of the individual cardiac cycles, wherein the second number is greater than the first number.

In accordance with certain embodiments, the feature of the signal, for which the measure of STV and the measure of LTV are determined over the measurement period, comprises a morphological feature, which comprises one of: an area under a curve of a QRS complex, R-wave, T-wave, ST-region, or evoked response; a maximum amplitude of a QRS complex, R-wave, T-wave, or evoked response; or a peak-to-peak amplitude of a QRS complex, R-wave, T-wave, or evoked response.

In accordance with certain embodiments, the feature of the signal, for which the measure of STV and the measure of LTV are determined over the measurement period, comprises a temporal feature, which comprises one of: RR interval duration; PR interval duration; QT interval duration; QRS complex duration; AR interval duration; PV interval duration; or evoked response duration.

In accordance with certain embodiments, each of the measure of STV and the measure of LTV in the feature of the signal over the measurement period is one of: a standard deviation of the feature; a standard deviation of the feature divided by an average of the feature; a difference between a maximum and a mean of the feature; a difference between a maximum and a minimum of the feature; a difference between a second maximum and a second mean of the feature; a difference between then Nth maximum and Nth mean of the feature; or any one of said differences divided by an average of the feature.

In accordance with certain embodiments, the apparatus further comprises an accelerometer that alone or in combination with the at least one processor is used to obtain posture information and activity information, wherein the at least one processor is further configured to: classify the patient as being asleep based on the posture information and the activity information; classify the patient as being awake based on at least one of the posture information or the activity information; enable the determining of the measure of STV and the measure of LTV that are used to detect the potential apnea event, in response to the patient being classified as being asleep; and disable the determining of the measure of STV and the measure of LTV that are used to detect the potential apnea event, in response to the patient being classified as being awake.

In accordance with certain embodiments, the at least one processor is further configured to determine whether the potential apnea event is a true apnea event or a false detection by analyzing a portion of the signal preceding the measurement period in which the potential apnea event was detected to determine whether a heart rhythm change likely caused the potential apnea event to be detected.

A method for monitoring for apnea, according to certain embodiments of the present technology, comprises: obtaining a signal indicative of cardiac electrical activity of a patient's heart; determining a measure of short-term variation (STV) and a measure of long-term variation (LTV) of a feature of the signal over a measurement period that includes a plurality of cardiac cycles; and detecting a potential apnea event in the measurement period based on the measure of STV and the measure of LTV in the feature; wherein the feature comprises one of a morphological feature or a temporal feature.

In accordance with certain embodiments, the method further comprises identifying individual cardiac cycles within the signal; and wherein the measure of STV is determined based on a first number of the individual cardiac cycles, and the measure of LTV is determined based on a second number of the individual cardiac cycles, wherein the second number is greater than the first number.

In accordance with certain embodiments, the method further comprises determining whether the potential apnea event that is detected is a true apnea event or a false detection by analyzing a portion of the signal preceding the measurement period in which the potential apnea event was detected to determine whether a heart rhythm change, a presence of a non-cardiac signal, or a change in the feature is due to a change in patient posture or patient activity likely caused the potential apnea event to be detected; and in response to determining that the potential apnea event is a true apnea event, storing or uploading information about the true apnea event so that the information can be accessed by a medical practitioner; wherein the heart rhythm change comprises at least one of: multiple cardiac rhythms comprising a pacing rhythm in conjunction with an intrinsic rhythm; one or more premature ventricular contractions; or one or more premature atrial contractions.

In accordance with certain embodiments, the detecting the potential apnea event occurs in response to the measure of LTV of the feature being greater than the measure of STV of the feature for at least the measurement period. In accordance with other embodiments, the detecting the potential apnea event occurs in response to both the measure of LTV of the feature being greater than the measure of STV for at least the measurement period, and the measure of STV of the feature being less that a specified threshold for at least the measurement period.

In accordance with certain embodiments, the feature of the signal, for which the measure of STV and the measure of LTV are determined over the measurement period, comprises a morphological feature, which comprises one of: an area under a curve of a QRS complex, R-wave, T-wave, ST-region, or evoked response; a maximum amplitude of a QRS complex, R-wave, T-wave, or evoked response; or a peak-to-peak amplitude of a QRS complex, R-wave, T-wave, or evoked response.

In accordance with certain embodiments, the feature of the signal, for which the measure of STV and the measure of LTV are determined over the measurement period, comprises a temporal feature, which comprises one of: RR interval duration; PR interval duration; QT interval duration; QRS complex duration; AR interval duration; PV interval duration; or evoked response duration.

In accordance with certain embodiments, each of the measure of STV and the measure of LTV in the feature of the signal over the measurement period is one of: a standard deviation of the feature; a standard deviation of the feature divided by an average of the feature; a difference between a maximum and a mean of the feature; a difference between a maximum and a minimum of the feature; a difference between a second maximum and a second mean of the feature; a difference between then Nth maximum and Nth mean of the feature; or any one of said differences divided by an average of the feature.

In accordance with certain embodiments, the method further comprises using an accelerometer to obtain posture information and activity information; classifying the patient as being asleep based on the posture information and the activity information; in response to classifying the patient as being asleep, enabling the determining of the measure of STV and the measure of LTV that are used for detecting the potential apnea event; classifying the patient as being awake based on at least one of the posture information or the activity information; and in response to classifying the patient as being awake, disabling the determining of the measure of STV and the measure of LTV that are used for detecting the potential apnea event.

In accordance with certain embodiments of the present technology, a non-transitory computer readable medium stores instructions to detect an apnea event that, when executed by a processor, causes the processor to perform operations, comprising: obtaining a signal indicative of cardiac electrical activity of a patient's heart; determining a measure of short-term variation (STV) and a measure of long-term variation (LTV) in a feature of the signal over a measurement period that includes a plurality of cardiac cycles; and detecting a potential apnea event in the measurement period based on the measure of STV and the measure of LTV in the feature; wherein the feature comprises one of a morphological feature or a temporal feature. The non-transitory computer readable medium can also include instructions that further cause the processor to perform other steps and features of the above summarized methods.

Certain embodiments of the present technology are directed to apparatuses, methods, and non-transitory computer readable medium storing instructions that can be used to classify a patient as either being asleep or awake. Such an apparatus can include an accelerometer and at least one processor. The accelerometer, alone or in combination with the at least one processor, is used to determine an activity level of a patient and a posture of the patient. The at least one processor is configured to: classify the patient as being asleep in response to both (i) the posture of the patient being recumbent or reclined for at least a sleep latency duration, and (ii) the activity level of the patient not exceeding an activity threshold for at least the sleep latency duration; and classify the patient as being awake in response to at least one of (iii) the posture of the patient being upright for at least an awake latency duration, or (iv) the activity level of the patient exceeding the activity threshold for at least the awake latency duration. In accordance with certain embodiments, the apparatus comprises an implantable medical device, such as an implantable pacemaker, an implantable cardiac defibrillator, or an implantable cardiac monitor.

In accordance with certain embodiments, the at least one processor of the apparatus is further configured to: detect the activity level of the patient over a period of time; produce a histogram based on the activity level of the patient over the period of time, the histogram including a plurality of bins each of which is associated with a different activity level and includes a respective number of activity counts; and determine the activity threshold based on the histogram.

In accordance with certain embodiments, the at least one processor of the apparatus is configured to: determine a total number of activity counts included in the histogram; determine the activity level corresponding to a specified percent of the total number of activity counts; and determine the activity threshold as being equal to the activity level corresponding to the specified percent of the total number of activity counts.

In accordance with certain embodiments, the at least one processor of the apparatus is configured to: determine one of a long term average (LTA) or a long term moving average (LTMA) of the activity level of the patient over a period of time; and determine the activity threshold as being equal to the one of the LTA or the LTMA of the activity level of the patient, or as being equal to the one of the LTA or the LTMA of the activity level of the patient plus a specified offset.

In accordance with certain embodiments, the one of the LTA or the LTMA changes over time, and thus, the activity threshold determined by the at least one processor also changes over time.

In accordance with certain embodiments, the at least one processor of the apparatus is further configured to: enable monitoring for apnea in response to the patient being classified as being asleep; and disable monitoring for apnea in response to the patient being classified as being awake. In accordance with certain embodiments, the at least one processor is further configured to: enable monitoring of sleep quality in response to the patient being classified as being asleep; and disable monitoring of sleep quality in response to the patient being classified as being awake.

Certain embodiments of the present technology are directed to a method comprising: determining an activity level of a patient; determining a posture of the patient; during a first period of time, classifying the patient as being asleep in response to both (i) the posture of the patient being recumbent or reclined for at least a sleep latency duration, and (ii) the activity level of the patient not exceeding an activity threshold for at least the sleep latency duration; and during a second period of time, classifying the patient as being awake in response to at least one of (iii) the posture of the patient being upright for at least an awake latency duration, or (iv) the activity level of the patient exceeding the activity threshold for at least the awake latency duration.

In accordance with certain embodiments, the determining the activity level of the patient and the determining the posture of the patient are performed using an accelerometer. In accordance with certain embodiments, the method is performed by an implantable medical device that includes the accelerometer.

In accordance with certain embodiments, the method further comprises: detecting the activity level of the patient over a period of time; producing a histogram based on the activity level of the patient over the period of time, the histogram including a plurality of bins each of which is associated with a different activity level and includes a respective number of activity counts; and determining the activity threshold based on the histogram.

In accordance with certain embodiments, the determining the activity threshold based on the histogram comprises: determining a total number of activity counts included in the histogram; determining the activity level corresponding to a specified percent of the total number of activity counts; and determining the activity threshold as being equal to the activity level corresponding to the specified percent of the total number of activity counts.

In accordance with certain embodiments, the method further comprises: determining one of a long term average (LTA) or a long term moving average (LTMA) of the activity level of the patient over a period of time; and determining the activity threshold as being equal to the one of the LTA or the LTMA of the activity level of the patient, or as being equal to the one of the LTA or the LTMA of the activity level of the patient plus a specified offset. In accordance with certain embodiments, the one of the LTA or the LTMA changes over time, and thus, the activity threshold also changes over time.

In accordance with certain embodiments, the method further comprises: enabling monitoring for apnea in response to the patient being classified as being asleep; and disabling monitoring for apnea in response to the patient being classified as being awake. Alternatively, or additionally, the method further comprises: enabling monitoring of sleep quality in response to the patient being classified as being asleep; and disabling monitoring of sleep quality in response to the patient being classified as being awake.

In accordance with certain embodiments of the present technology, a non-transitory computer readable medium stores instructions that when executed by a processor cause the processor to perform operations, comprising: determining an activity level of a patient; determining a posture of the patient; classifying the patient as being asleep in response to both (i) the posture of the patient being recumbent or reclined for at least a sleep latency duration, and (ii) the activity level of the patient not exceeding an activity threshold for at least the sleep latency duration; and classifying the patient as being awake in response to at least one of (iii) the posture of the patient being upright for at least an awake latency duration, or (iv) the activity level of the patient exceeding the activity threshold for at least the awake latency duration. The non-transitory computer readable medium can also include instructions that further cause the processor to perform other steps and features of the above summarized methods.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structure and method of operation may best be understood by referring to the following description and accompanying drawings, in which similar reference characters denote similar elements throughout the several views:

FIG. 3 illustrates a general method for detecting apnea events, in accordance with an embodiment of the present technology.

FIG. 7B shows example pseudocode that can be used to implement the method summarized with reference to the flow diagram of FIG. 7A.

FIG. 8B shows example pseudocode that can be used to implement the method summarized with reference to the flow diagram of FIG. 8A.

DETAILED DESCRIPTION

Technology is presented for electrogram (EGM) or electrocardiogram (ECG) based SAS detection. The technology provides a monitoring algorithm that is time-domain based in its computational approach and does not require extra circuitry for implementation in a surface or implanted device. The EGM or ECG features are easily extracted, and the computational requirement has minimal impact on the battery longevity when used in IMDs or surface mounted devices. In one aspect, the technology is an apparatus and method which detects potential apnea events (an apnea or hypopnea event) using a signal indicative of cardiac electrical activity of a patient's heart, such as in EGM or ECG signal. The technology uses variations in one or more morphological or temporal features of the signal over a number of cardiac cycles to detect a potential apnea event in a measurement period. The technology then checks for a number of factors which could result in a false detection of an apnea event and if such factors are not present, an apnea event is recorded. The technology may be included in an IMD or surface mounted device which may include aspects of the technology to perform the detection and reporting methods described herein in real-time as a patient sleeps, or may provide data to another device which then analyzes the data after recording.

Figure 1:
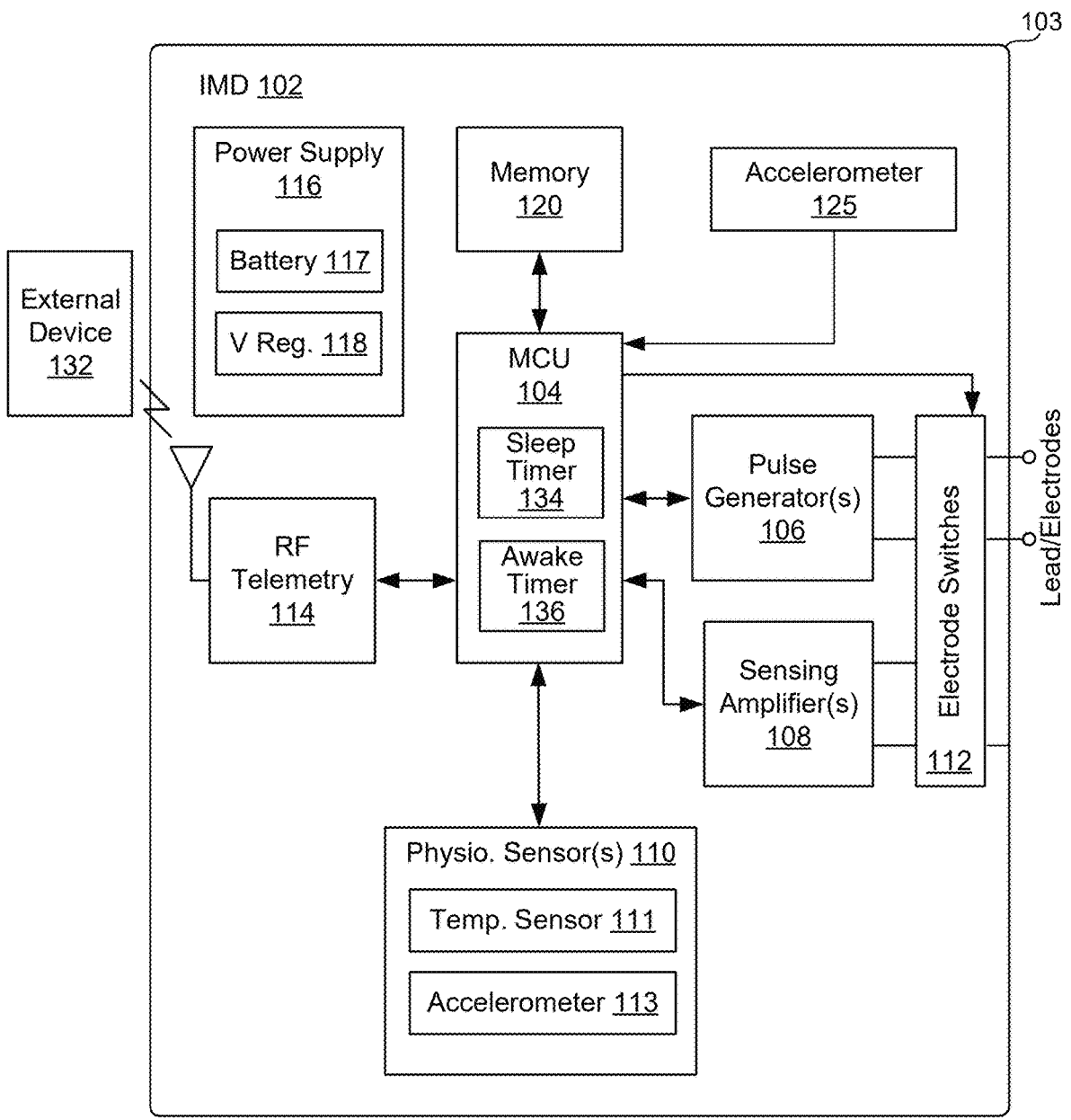
FIG. 1 is a block diagram of an implantable medical device suitable for implementing the present technology.

FIG. 1 is a block diagram of an example IMD 102, which can be a leadless cardiac pacemaker (LCP), traditional pacemaker, implantable cardiac defibrillator (ICD), neurostimulator, insertable cardiac monitor, or the like. The IMD 102 is shown as including a microcontroller unit (MCU) 104, pulse generator(s) 106, sensing amplifier(s) 108, physiologic sensor(s) 110, electrode switches 112, an RF telemetry module 114, a power supply 116, an accelerometer 125 and memory 120.

The MCU 104 can control various modes of stimulation therapy. As is well known in the art, the MCU 104 (also referred to herein as a control unit or controller) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the MCU 104 includes the ability to process or monitor input signals (data) as controlled by a program code stored in a designated block of memory. The details of the design and operation of the MCU 104 are not critical to the technology. Rather, any suitable MCU 104 that includes at least one processor may be used that carries out the functions described herein. The use of microprocessor-based control circuits for performing timing and data analysis functions are well known in the art. In certain embodiments, the MCU 104 is used to implement a sleep timer 134 and an awake timer 136, as shown in FIG. 1. Such timers 134, 136 can alternatively be implemented using circuitry that is external to the MCU 104, but in communication with the MCU 104. The use of such timers 134, 136 are discussed below with reference to FIGS. 7A-9.

Where the IMD 102 is a cardiac stimulation device, the pulse generator(s) 106 can include an atrial pulse generator and a ventricular pulse generator that generate pacing stimulation pulses for delivery to cardiac tissue via electrodes. Such electrodes can be included on leads, or can be on or adjacent a housing 103 of the IMD 102, e.g., if the IMD 102 is an LCP. Where more than two electrodes are available for delivering stimulation pulses, the electrode switches 112 can be used to select specific combinations of electrodes under the control of the MCU 104. It is understood that in order to provide stimulation therapy in one or more of the four chambers of the heart, atrial and/or ventricular pulse generators (e.g., 106) may include dedicated, independent pulse generators, multiplexed pulse generators or shared pulse generators. The pulse generator(s) 106 are controlled by the MCU 104 via appropriate control signals to trigger or inhibit the stimulation pulses. Where the IMD 102 is a neurostimulator, the pulse generator(s) 106 can produce stimulation pulses that are for use in performing spinal cord stimulation (SCL), dorsal root ganglion (DRG) stimulation, deep brain stimulation (DBS), and/or the like. In the below description, unless stated otherwise, it will be assumed that the IMD 102 is a cardiac stimulation device.

Where the IMD 102 is a cardiac stimulation device, the MCU 104 can include a timing control module to control the timing of the stimulation pulses, including, but not limited to, pacing rate, atrioventricular (AV) delay, interatrial conduction (AA) delay, interventricular conduction (VV) delay and/or intraventricular delay (e.g., LV1-LV2 delay). The timing control module can also keep track of the timing of refractory periods, blanking intervals, noise detection windows, evoked response detection windows, alert intervals, marker channel timing, etc., which is well known in the art. The MCU 104 can also include an apnea detector that can be used in accordance with the methods discussed herein. The MCU 104 can also include a capture detection module and/or a morphology detection module. Depending upon the implementation, the various components of the MCU 104 may be implemented as separate software modules or the modules may be combined to permit a single module to perform multiple functions. In addition, although described as being components of the MCU 104, some or all of the above discussed modules may be implemented separately from the MCU 104, e.g., using one or more application specific integrated circuits (ASICs) or the like.

The electrode switches 112, which can also be referred to as switching circuitry 112, includes a plurality of switches for connecting the desired electrodes to the appropriate I/O circuits, thereby providing complete electrode programmability. Accordingly, the switching circuitry 112, in response to a control signal from the MCU 104, determines the polarity of the stimulation pulses (e.g., unipolar, bipolar, combipolar, etc.) by selectively closing the appropriate combination of switches (not shown) as is known in the art. The switching circuitry 112 can also switch among the various different combinations of electrodes.

The sensing amplifier(s) 108 can include, e.g., atrial and/or ventricular sensing amplifiers that are selectively coupled to various combinations of electrodes to provide for various different sensing vectors that can be used, e.g., for detecting the presence of cardiac activity in one or more of the four chambers of the heart. Accordingly, the sensing amplifier(s) 108 can include dedicated sense amplifiers, multiplexed amplifiers or shared amplifiers. The switching circuitry 112 determines the "sensing polarity" of the cardiac signal by selectively closing the appropriate switches, as is also known in the art. In this way, a clinician may program the sensing polarity independent of the stimulation polarity. Each sensing amplifier 108 can employ one or more low power, precision amplifiers with programmable gain and/or automatic gain control, bandpass filtering, and a threshold detection circuit, as known in the art, to selectively sense the cardiac signal of interest. The automatic gain control enables the IMD 102 to deal effectively with the difficult problem of sensing the low amplitude signal characteristics of atrial or ventricular fibrillation. The outputs of the sensing amplifier(s) 108 are connected to the MCU 104 which, in turn, is able to trigger or inhibit the one or more pulse generator(s) 106 in a demand fashion in response to the absence or presence of cardiac activity in the appropriate chambers of the heart.

For apnea detection, the MCU 104 utilizes the sensing amplifier(s) 108 to sense cardiac signals to acquire a cardiac signal. As used in this section "sensing" is reserved for the noting of an electrical signal, and "detection" is the processing of these sensed signals and noting the presence of an apnea event or some other event being monitored for.

Although not specifically shown in FIG. 1, cardiac signals can also be applied to the inputs of an analog-to-digital (A/D) data acquisition system that is configured to acquire intracardiac electrogram signals, convert the raw analog data into a digital signal, and store the digital signals for later processing and/or telemetric transmission to an external programmer or a bedside monitor or personal advisory module (PAM). The data acquisition system can be coupled to various leads and/or electrodes through the switching circuitry 112 to sample cardiac signals across any pair of desired electrodes. The MCU 104 is further coupled to the memory 120 by a suitable data/address bus, or the like, wherein the programmable operating parameters used by the MCU 104 are stored and modified, as required, in order to customize the operation of IMD 102 to suit the needs of a particular patient. Such operating parameters define, for example, the amplitude or magnitude, pulse duration, electrode polarity, for both pacing pulses and impedance detection pulses as well as pacing rate, sensitivity, apnea detection criteria, and the amplitude, waveshape and vector of each pacing and shocking pulse to be delivered to the patient's heart within each respective tier of therapy. Other pacing parameters include base rate, rest rate and circadian base rate.

Advantageously, the operating parameters of the IMD 102 may be non-invasively programmed into the memory 120 through an RF telemetry circuit 114 in telemetric communication with an external device or bedside monitor 132, such as a programmer, transtelephonic transceiver or a diagnostic system analyzer. The RF telemetry circuit 114, which can also be referred to as an RF communication subsystem, is activated by the MCU 104 by a control signal. The RF telemetry circuit 114 advantageously allows intracardiac electrograms and status information relating to the operation of the IMD 102 (as contained in the MCU 104 or memory 120) to be sent to the external device 132 through an established communication link. An internal warning device, not specifically shown, may be provided for generating perceptible warning signals to the patient via vibration, voltage or other methods.

The memory 120 may include instructions operable to cause the MCU 104 to perform the methods described herein. In one embodiment, memory 120 may comprise a non-volatile, non-transitory computer readable medium and/or volatile memory containing such instructions. Alternatively, the MCU 104 may include an internal computer readable medium or memory including the instructions.

The physiologic sensors 110 can include a temperature sensor 111, an accelerometer 113, and/or other types of physiologic sensors, commonly referred to as a "rate-responsive" sensor because they can be used to adjust pacing stimulation rate according to the exercise state of the patient. However, the physiological sensor(s) 110 may further be used to detect changes in cardiac output, changes in the physiological condition of the heart, or diurnal changes in activity (e.g., detecting sleep and wake states) and to detect arousal from sleep. While shown as being included within the IMD 102, it is to be understood that one or more of the physiologic sensor(s) 110 may also be external to the IMD 102, yet still be implanted within or carried by the patient. A common type of rate responsive sensor is an activity sensor incorporating an accelerometer or a piezoelectric crystal, which is mounted within the housing 103 of the IMD 102. Other types of physiologic sensors are also known, for example, sensors that sense the oxygen content of blood, respiration rate and/or minute ventilation, pH of blood, ventricular gradient, stroke volume, cardiac output, contractility, etc.

The power supply 116, which can include a battery 117 and a voltage regulator 118, provides operating power to all of the circuits or subsystem shown in FIG. 1. The specific type of battery 117 included in the IMD 102 can vary depending on the capabilities of IMD 102. If the IMD 102 only provides low voltage therapy, a lithium iodine or lithium copper fluoride cell typically may be utilized as the battery 117. If the IMD 102 provides shocking therapy, the battery 117 should be capable of operating at low current drains for long periods, and then be capable of providing high-current pulses (for capacitor charging) when the patient requires a shock pulse. The battery 117 should also have a predictable discharge characteristic so that elective replacement time can be detected. Accordingly, appropriate batteries are employed. One or more voltage regulators 118 can step up or step down a voltage provide by the battery 117 to produce one or more predetermined voltages useful for powering the various circuits or subsystems of the IMD 102.

The IMD 102 can include additional and/or alternative types of circuits or subsystems, not specifically shown in FIG. 1. For example, the IMD 102 can also include an impedance measurement circuit that can be used for providing lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. Such an impedance measurement circuit can be coupled to the switching circuitry 112 so that any desired combination of electrodes may be used.

The above described IMD 102 was described as an exemplary cardiac stimulation or detection device. One of ordinary skill in the art would understand that embodiments of the present technology can be used with alternative types of implantable devices. Accordingly, embodiments of the present technology should not be limited to use only with the above described device.

The RF telemetry circuit 114 can be the Bluetooth Low Energy (BLE) radio, or some other RF communication subsystem, that is implemented in an RF integrated circuit (IC). The remaining set of circuits or subsystems of the IMD 102 shown in FIG. 1, or just a subset thereof, can be implemented in a custom application specific IC (ASIC), which can also be referred to as a custom chip. In other words, the terms IC and chip are used interchangeably herein. Depending on the specific IMD, there may be additionally IC's. The custom IC can host the IMD's application and have all the associated circuits for sensing, pacing, high voltage (HV) therapy, etc. The RF chip, which is used to provide RF communication, can include a high-speed (aka high frequency) crystal oscillator. The connection between the RF chip and the custom chip is typically a standard serial interface, such as serial peripheral interface (SPI) and a few general-purpose input-outputs (GPIO), but can alternatively or additionally include a parallel interface.

It is well known that each cardiac cycle represented within an EGM or an electrocardiogram (ECG) typically includes a P-wave, followed by a QRS complex, followed by a T-wave, with the QRS complex including Q-, R-, and S-waves. The P-wave is caused by depolarization of the atria. This is followed by atrial contraction, which is indicated by a slight rise in atrial pressure contributing to further filling of the ventricle. Following atrial contraction is ventricular depolarization, as indicated by the QRS complex, with ventricular depolarization initiating contraction of the ventricles resulting in a rise in ventricular pressure until it exceeds the pulmonary and aortic diastolic pressures to result in forward flow as the blood is ejected from the ventricles. Ventricular repolarization occurs thereafter, as indicated by the T-wave and this is associated with the onset of ventricular relaxation in which forward flow stops, the pressure in the ventricle falls below that in the atria at which time the mitral and tricuspid valves open to begin to passively fill the ventricle during diastole. The terms EGM, EGM signal, and EGM waveform are used interchangeably herein. Similarly, the terms ECG, ECG signal, and ECG waveform are used interchangeably herein. Both ECG and EGM signals are signals indicative of electrical activity of a patient's heart, which can also be referred to as cardiac electrical signals, or the like.

The R-wave is the largest wave in the QRS complex, and it often identified by comparing samples of an EGM or ECG to an R-wave threshold. Various measurements can be obtained based on the EGM or ECG waveform, including measurements of R-R intervals, where an R-R interval is the duration between a pair of consecutive R-waves.

As will be described in additional detail below, certain embodiments of the present technology described herein provide for sleep apnea discrimination by distinguishing between irregular patterns in the variability of the morphology of a QRS complex. Although the present technology will be described with respect to use of variability of the R-wave, any of the morphological features of the QRS complex may be used in accordance with the present technology. For example, where elements of the R-wave are described herein, one may substitute use of the T-wave morphology in the analysis.

Figure 2:
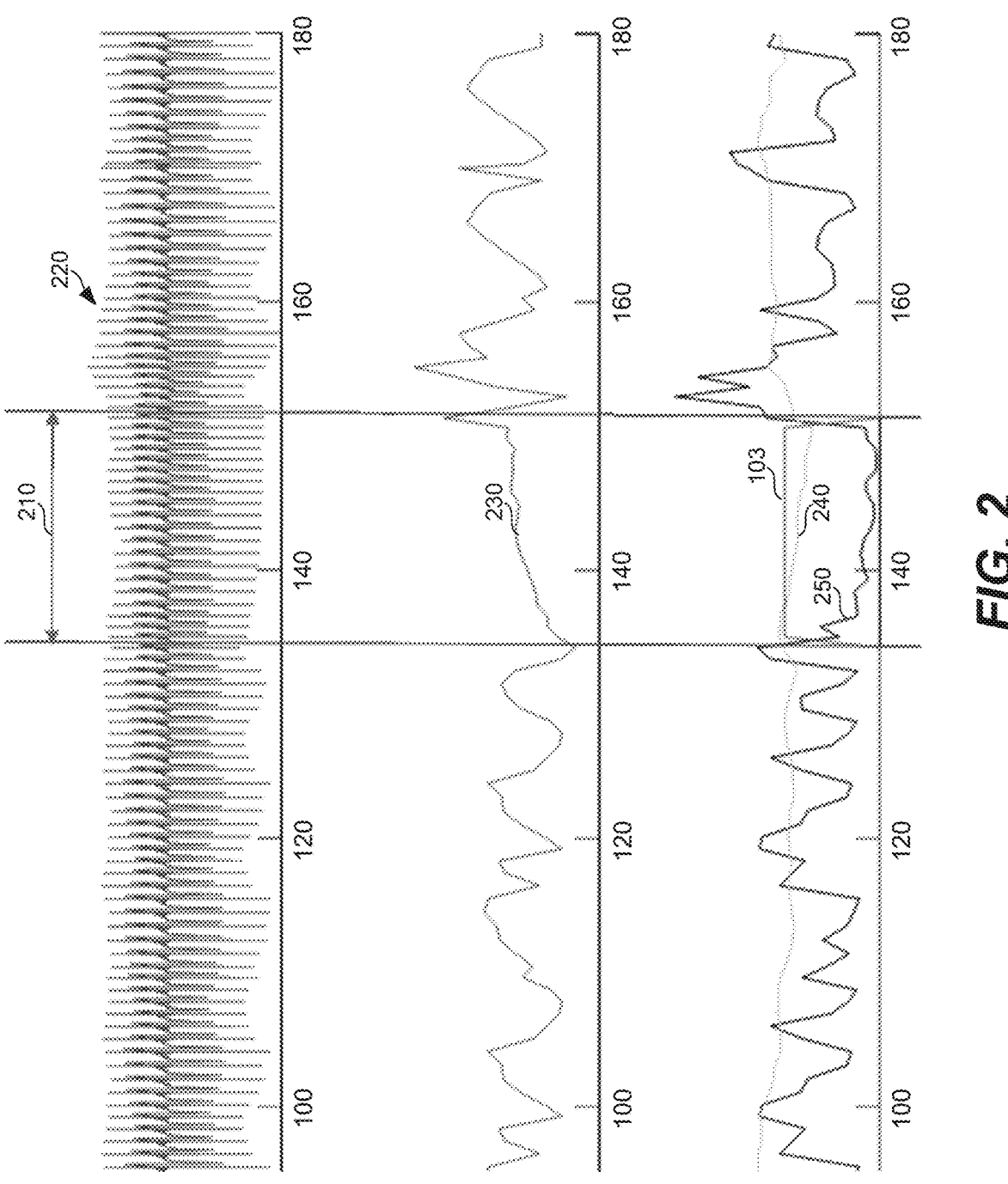
FIG. 2 illustrates an EGM segment, a plot of the R-wave amplitude variability of the signal in the segment, a plot of the short-term variability (STV) of peak to peak (P2P) R-wave amplitude of the signal in the segment, and a plot of the long-term variability (LTV) of P2P R-wave amplitude of the signal in the segment.

FIG. 2 at the top illustrates an example EGM segment 220 of approximately eighty (80) seconds (between time markers 100 and 180 seconds). FIG. 2 in the middle illustrates a plot 230 of the R-wave amplitude variability of the signal in the segment 220. FIG. 2 at the bottom illustrates a plot 250 of the short-term variability (STV) of peak-to-peak (P2P) R-wave amplitude of the signal in the EGM segment 220, and a plot 240 of the long-term variability (LTV) of P2P R-wave amplitude of the signal in the EGM segment 220. Certain embodiments of the present technology take advantage of the realization that R-wave amplitude variability changes during periods of reduced or absent airflow. Thus, the significant reduction of R-wave amplitude variability in window 210 between the 135 and 155 second time markers indicates a no breathing phase (NBP), which can also be referred to as a non-breathing period (NBP). This reduction of R-wave amplitude variability in window 210 is a discernable change from the R-wave amplitude variation during normal breathing (prior to window 210 and after window 210) and may indicate a potential apnea event. The term short-term variability (STV) can also be referred to interchangeably herein as the short-term variation (STV), or a measure of STV. Similarly, the term long-term variability (LTV) can also be referred to herein as the long-term variability (LTV), or a measure of LTV.

Certain embodiments of the present technology use this characteristic of the signal to detect this NBP by comparing the STV to the LTV of the feature of the signal. In particular, in certain embodiments a comparison of STV and LTV of a feature of the R-wave is used to detect a non-breathing period indicating a potential apnea event. In normal breathing, the STV of the R-wave amplitude crosses LTV periodically, whereas the STV of the R-wave amplitude stays below LTV during the entire duration of a non-breathing period. In addition, the STV is much lower in amplitude during a non-breathing period as compared to a normal breathing period. These two characteristics of the signal are used to detect potential apnea events.

Although the present technology is described in one aspect as using a comparison of STV and LTV of R-wave amplitude, other alternatives may be used to determine a potential apnea event. For example, one may use a coarser determination of determining a potential apnea event when STV of the R-wave amplitude (or T-wave amplitude or other morphological feature) drops below a pre-defined threshold, without comparing the STV to the LTV.

FIG. 3 illustrates a general method for detecting apnea events, in accordance with certain embodiments of the present technology. At step 300, a signal indicative of cardiac electrical activity of a heart is obtained. Such a signal can be an electrocardiogram (ECG) or an electrogram (EGM), depending upon whether the signal is obtained by a non-implanted device or an implanted device. For example, the signal can be an EGM obtained using an IMD, such as the IMD 100 described above with reference to FIG. 1. The signal may be a measure of an intrinsic rhythm or a ventricular pacing rhythm. In alternative embodiments, an external (i.e., non-implanted) medical device such as a Holter monitor may be utilized to obtain an ECG. In certain embodiments, where IMD 100 is utilized, the EGM signal is only obtained while a patient is sleeping (or at least likely to be sleeping) as determined by the MCU 104 based on a signal received from the accelerometer 125 that indicates the patient is at rest. In other embodiments, the EGM signal may also be obtained during one or more periods of time when the patient is not sleeping, but the EGM signal is only used to detect a potential apnea event when it is determined that the patient is likely to be sleeping. More generally, in certain embodiments, a method for monitoring for apnea is only performed when it is determined that a patient is sleeping, or at least likely to be sleeping. Various techniques for determining that a patient is sleeping (or at least likely to be sleeping) may be utilized including, but not limited to, the time of day, and/or the techniques described below with reference to FIG. 7A-12.

At step 310, there is a determination of at least one measure of variation in a feature of the signal (e.g., EGM or ECG) during a measurement period that includes a plurality of cardiac cycles. The measurement period may vary, but in one embodiment the measurement period has a duration of about 10 seconds. (Ten seconds without breathing is the period of time generally recognized as evincing an SAS event.) The use of shorter or longer measurement periods are also possible and within the scope of the embodiments described herein, although it is preferred that the measurement period be at least 10 seconds. The feature(s) for which at least one measure of variation is determined can be a morphological feature and/or a temporal feature. As noted above, in some embodiments, the at least one measure of variation includes both the STV and the LTV of the R-wave amplitude, which is an example of a morphological feature, but other measures of variations and/or other morphological features may alternatively or additionally be used. Such other morphological features may include an area under a curve of a QRS complex, R-wave, T-wave, or ST-region; a maximum amplitude of a QRS complex, R-wave, or T-wave; or a peak-to-peak (P2P) amplitude of a QRS complex, R-wave, or T-wave, but are not limited thereto. Where a patient's heart is paced, the morphological feature(s) can correspond to morphological features of paced cardiac cycles, such as, but not limited to, the amplitude, peak-to-peak (P2P) amplitude, and/or area under the curve of an evoked response. Both short-term and long-terms measures of variation (STV and LTV) can be determined for one or more of the above mentioned morphological features, and compared to one another and/or to respective thresholds, as explained in more detail below. Instead of (or in addition to) determining at least one measure of variation in one or more morphological features of the signal during the measurement period (that includes a plurality of cardiac cycles), at least one measure of variation can be determined in one or more temporal features of the signal, such as, but not limited to, RR interval durations, PR interval durations, QRS durations, and/or QT interval durations. Where a patient's heart is paced, the temporal feature(s) can correspond to temporal features of paced cardiac cycles, such as, but not limited to, AR interval durations, PV interval durations, or evoked response durations. The measure(s) of variation in the feature of the signal can be one or more of a standard deviation of the feature, a standard deviation of the feature divided by an average of the feature, a difference between a maximum and a mean of the feature, a difference between a maximum and a minimum of the feature, and/or a difference between a second maximum and a second mean of the feature (or a difference between then Nth maximum and Nth mean of the feature). The measure(s) of variation can alternatively At step 320, a potential apnea event in the measurement period is detected based on the at least one measure of variation in the feature. The feature may be a morphological feature or a temporal feature, as noted above. Additional details of how steps 310 and 320 can be performed, in accordance with certain embodiments, are described below in the discussion of FIGS. 4A-4C. However, in general, a potential apnea event is detected when two measures of variation in one or more features of the signal (obtained at step 300) are compared, or at least one measure of variation falls below one or more respective specified thresholds.

At step 330, if a potential apnea event is detected, a determination of whether the potential apnea event is a true apnea event is made by analyzing a portion of the signal preceding the measurement period. In other words, at step 330 the potential apnea event can be validated as being a true apnea event, or can be rejected as being a false positive. In certain embodiments, step 330 is optional. The detection of a potential apnea event using the present technology (at instances of step 320) may result from other changes in cardiac rhythm resulting from multiple cardiac rhythms such as a pacing rhythm in conjunction with an intrinsic rhythm, one or more premature ventricular contractions (PVCs), or one or more premature atrial contractions (PACs). In other words, at step 330 there is a determination of whether there was a false positive detection at step 320, wherein such a false positive detection may have occurred due to one or more PVC or PACs, and/or due to a patient's heart activating both intrinsically and in response to pacing during the measurement period.

Figure 4A:
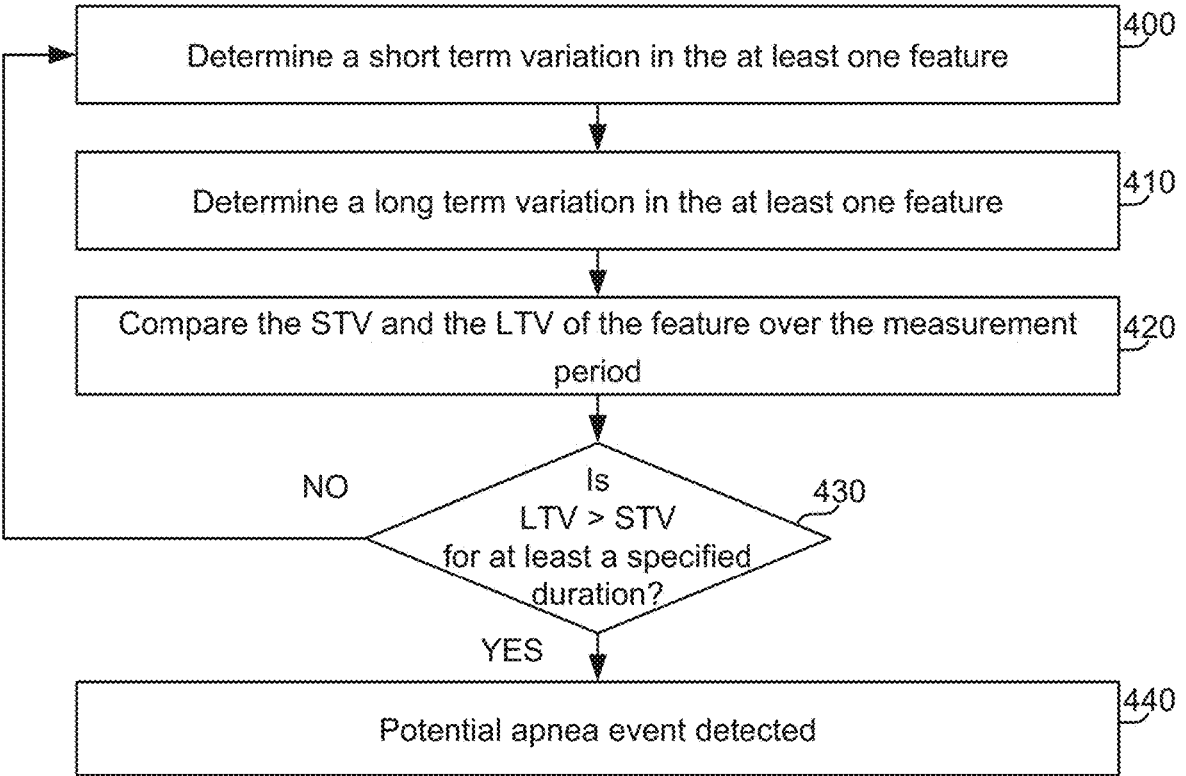
FIG. 4A illustrates one method for performing steps 310 and 320 of FIG. 3, in accordance with an embodiment of the present technology.

FIG. 4A illustrates one method for performing steps 310 and 320 of FIG. 3. At step 400, a STV in the at least one feature is determined. In one embodiment, feature for which the STV is determined is the peak-to-peak amplitude of an R-wave over three beats, but more or fewer beats may be used (so long as at least two beats are used). At step 410, an LTV in the at least one feature (e.g., peak-to-peak R-wave amplitude) is determined over twenty-five (25) beats, but more or fewer beats may be used. In steps 400 and 410, one or more measure(s) of variation can be determined for alternative and/or additionally morphological feature(s) besides the peak-to-peak amplitude for R-waves. Steps 400 and 410 show one method of performing step 310 of FIG. 3.

Once the STV and the LTV are determined at instances of steps 400 and 410, a comparison of the STV and LTV is made at step 420, to determine whether the LTV is greater than the STV for at least a specified duration. In one embodiment, the specified duration is a minimum of ten (10) seconds. A ten second duration is chosen because a single apnea/hypopnea event (AHE) is defined as reduced or absent airflow for a duration of 10 seconds. Thus, the method may use a minimum of ten seconds during which STV is lower than LTV to determine whether a potential apnea event has occurred.

At step 430, if the LTV is greater than the STV over the measurement window, a potential apnea event is determined to be detected at 440. If over a window of at least ten seconds the LTV is greater than the STV, the method moves to determine whether the potential apnea event is an actual apnea event, and ensure that the potential apnea event is not caused by some other cardiac issue.

Figure 4B:
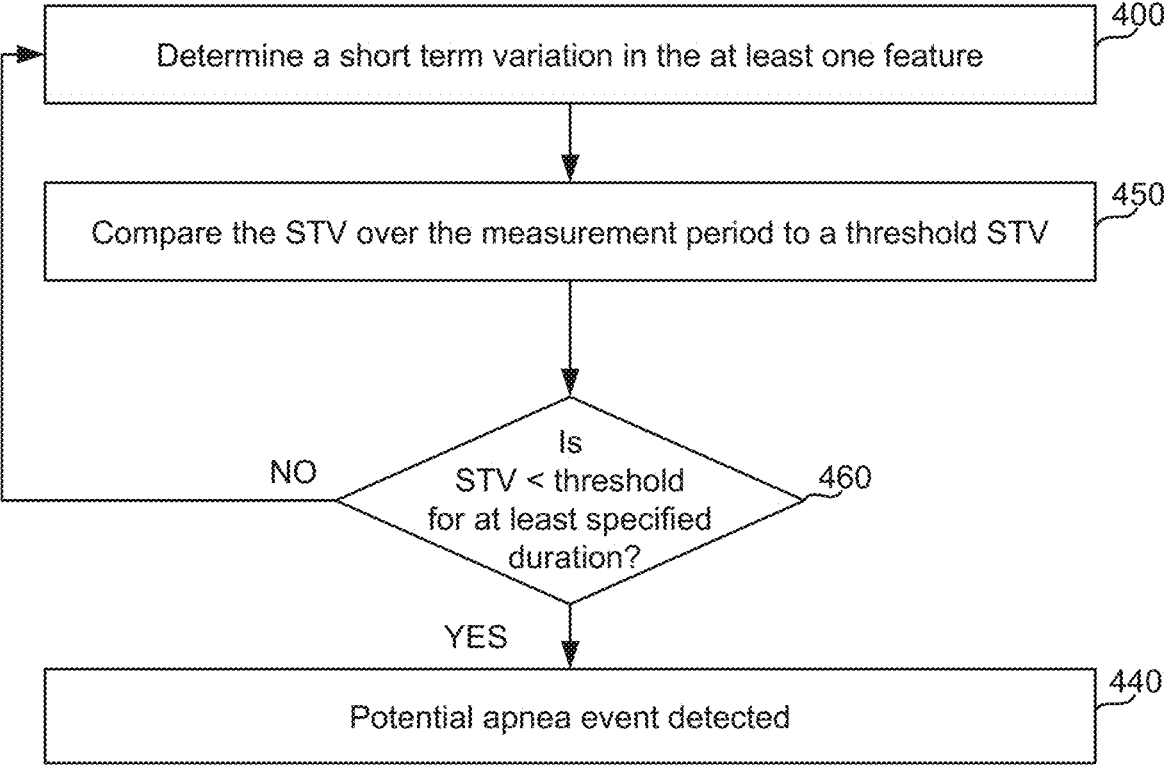
FIG. 4B illustrates another method for performing steps 310 and 320 of FIG. 3, in accordance with an embodiment of the present technology.

In alternative embodiments, the STV alone may be used to determine a potential apnea event. FIG. 4B illustrates one such embodiment. In FIG. 4B, like reference numbers indicate like steps to those in FIG. 4A. Step 400 is identical to step 400 of FIG. 4A where a STV in the at least one feature is determined. In one embodiment, feature for which the STV is determined is the peak-to-peak amplitude of an R-wave over three beats, but more or fewer beats may be used. At step 460, the STV is compared to a threshold value. At 460, if the STV is below the threshold value for the measurement period (for example, ten seconds), a potential apnea event is recognized at step 440. The threshold may be an absolute threshold or a variable threshold which may be a percentage of the STV for a period prior to the measurement period, a percentage of the LTV prior to the measurement period, or a percentage of the average STV over some period of the signal prior to the measurement period.

Figure 4C:
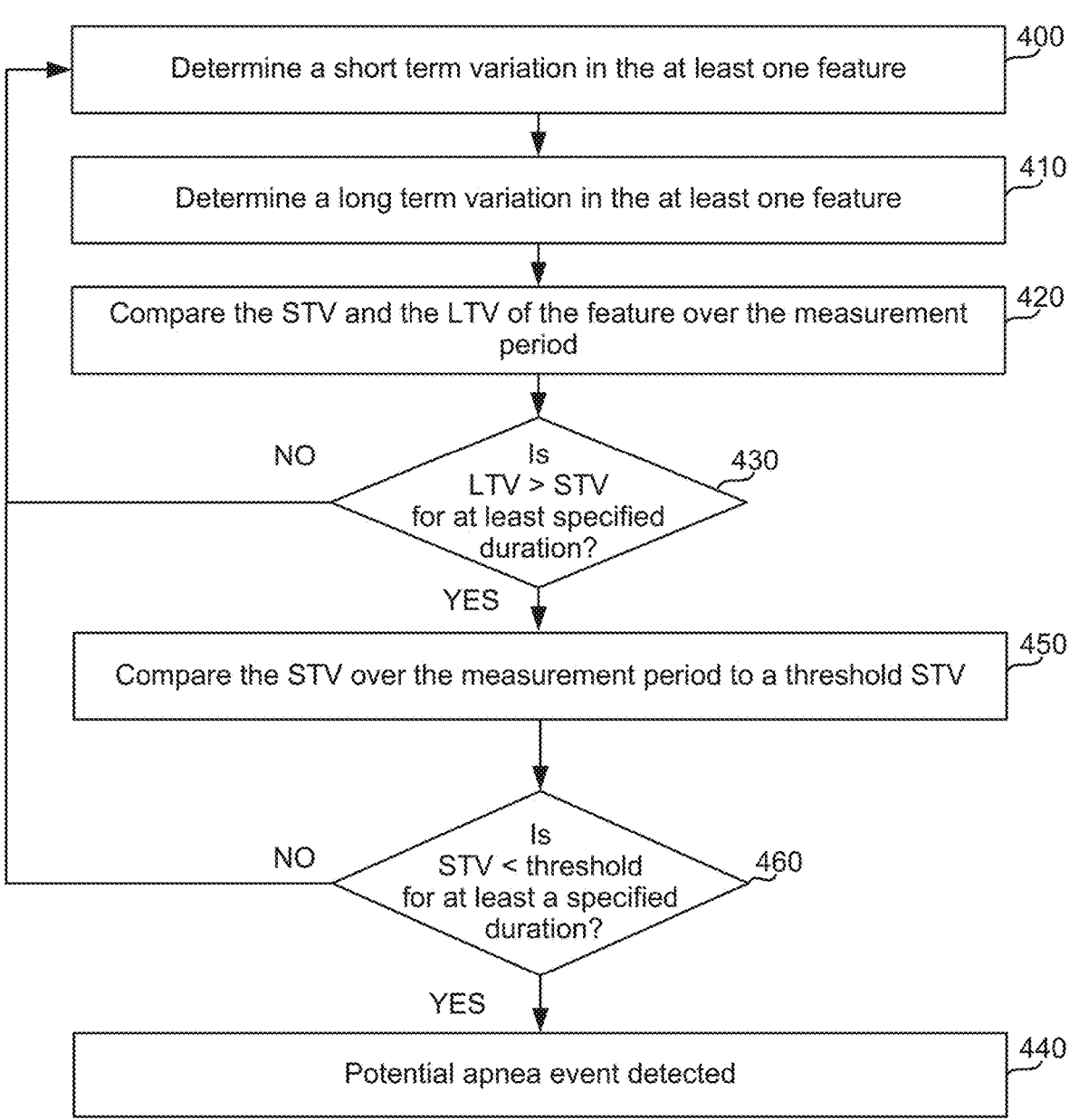
FIG. 4C illustrates yet another method for performing steps 310 and 320 of FIG. 3, in accordance with an embodiment of the present technology.

In yet another alternative, both a comparison of the LTV to the STV during the measurement period and a comparison of the STV to a threshold may be used to determine an apnea event, as illustrated in FIG. 4C. In FIG. 4C, like reference numbers indicate like steps to those in FIG. 4A and FIG. 4B. In FIG. 4C, the comparison at step 430 and the comparison at step 460 may be reversed in order.

Although the above description describes intrinsic pacing, the technology is operable in patients having active ventricular or V-pacing. In another embodiment, when a patient is known to have a pacemaker and is subject to V-pacing, the morphological feature may be measured by an area under the curve calculation of the morphological feature.

The above description uses an STV of three beats, but as few as two beats may comprise a period for determining an STV. The above description uses twenty-five beats for an LTV, but any number greater than the number of beats used for the STV may be used for the LTV. In one embodiment, two-times the number of beats used to determine the STV may be used to determine the LTV (i.e. if three beats is used to determine the STV, an LTV may be determined with six beats).

In one embodiment, the R-wave feature is measured over a time window measuring between 60 msec and 200 msec from an R-wave marker in the ECG signal, where the peak-to-peak minimum of the R-wave marker is subtracted from the maximum of the marker. When the feature is measured from a V-pacing morphology, the feature may be measured from the average under the curve between 0 msec from the initial V-pacing marker to 200 msec from the V-pacing marker. The average under the curve is calculated by summing the absolute values of the feature over the measurement window less the value of the feature at the start of the window.

Each of the long and short-term variability can be calculated as the standard deviation of the feature (R-wave amplitude in this example) divided by the average value of the feature. As noted above, for STV, the calculation can be performed over three beats and for LTV the calculation can be performed over twenty-five beats, in one embodiment.

During an episode of an arrhythmia, temporal features (e.g., RR interval durations, PR interval durations, QRS durations, and/or QT interval durations) of a signal (e.g., an EGM or ECG signal) indicative of cardiac electrical activity may be influenced by the arrhythmia, and temporal features of the EGM/ECG signal that may be useful for detecting an apnea event may be masked by the arrhythmia. Accordingly, in at least in one embodiment, during an arrhythmic episode, the feature(s) of the ECG/EGM for which measures of STV and/or LTV are determined and compared to one another (e.g., at steps 400, 410, and 420) or to a respective threshold (e.g., at step 450), for the purpose of detecting a potential sleep apnea event (e.g., at step 440 or 450), should be one or more morphological feature(s), rather than one or more temporal feature(s). In other words, in accordance with certain embodiments of the present technology, the usage of temporal feature(s) for the purpose of detecting a potential apnea event, are excluded upon and during an arrhythmia detection.

Figure 5:
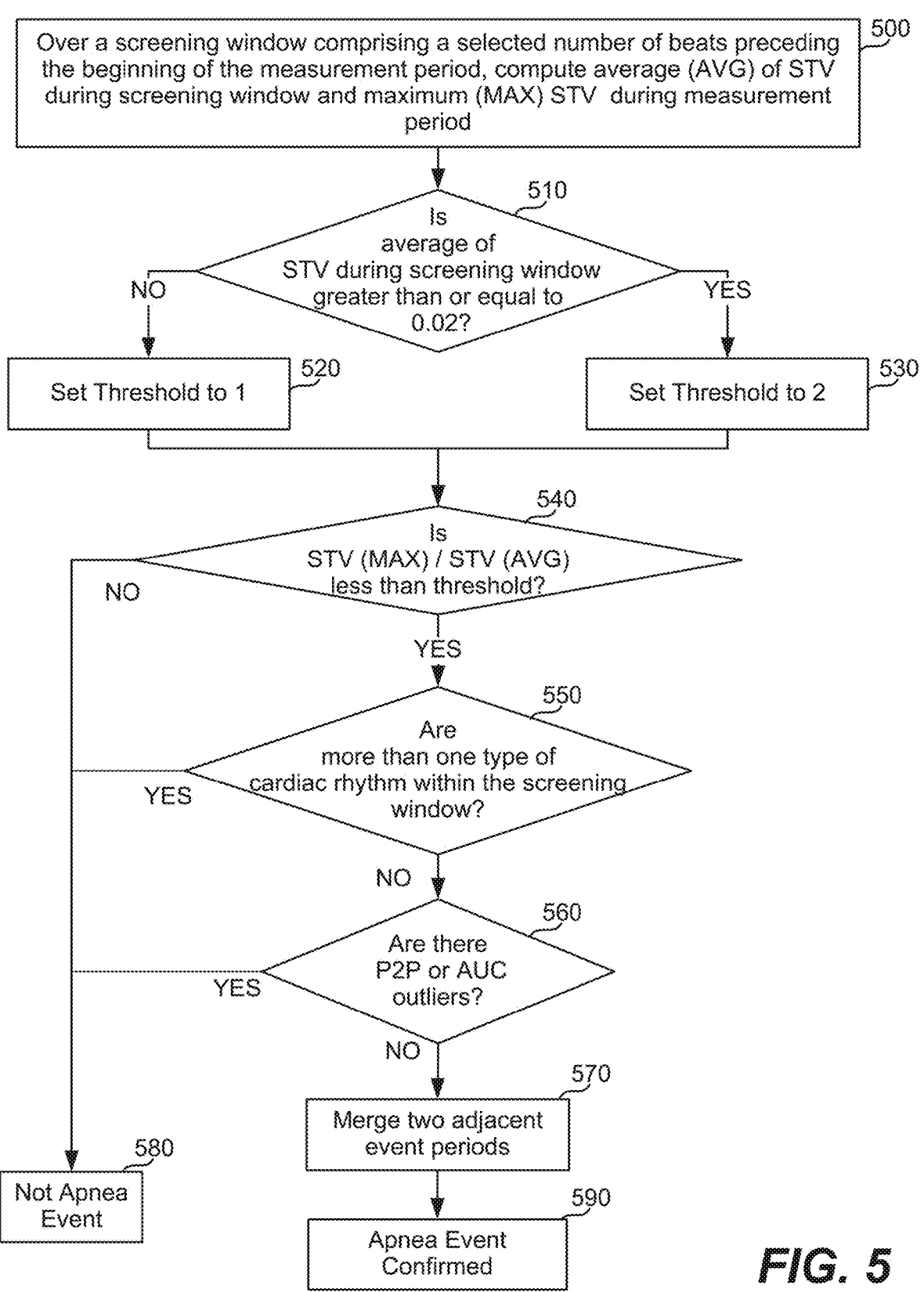
FIG. 5 illustrates one method for performing step 330 of FIG. 3, in accordance with an embodiment of the present technology.

FIG. 5 illustrates one method for performing step 330 of determining whether the potential apnea event is a true apnea event or a false detection by analyzing a portion of the signal preceding the measurement period. In the method of FIG. 5, the STV in the measurement period is compared against a threshold value. The threshold varies (between one (1) and two (2) in one embodiment) depending on the STV during the screening window. (As noted above, the STV can be the standard deviation of the feature (R-wave amplitude in this example) divided by the average value of the feature in the screening window.) In one embodiment, a screening window comprises the twenty-five (25) beats which immediately precede the measurement period. The screening window may be set at the same number of beats as the LTV (25 in the above description) such that if the LTV is measured over more or fewer beats, the screening window is set at the same number of beats. Alternatively, the screening window may be set at a different number of beats than the number of beats in the LTV calculation.

At step 500, over a screening window comprising a selected number of beats (e.g., twenty-five beats) preceding the beginning of the measurement period, the average of the STV (AVG) during screening window and a maximum of the STV (MAX) during the measurement period are calculated.

At step 510, if the average of STV (AVG) during screening window is greater than or equal to 0.02 seconds then the apnea detection threshold is set to a first threshold having a numerical value of two (2) at step 520. If the average of the STV during the screening window is less than 0.02 seconds, then the apnea detection threshold is set to a second threshold having a numerical value of one (1) at step 530. Thus, the threshold for comparison of STV to LTV may vary based on the average and maximum of the STV during the screening window.

At step 540, a determination is made as to whether the maximum of the STV during the measurement window (STV (MAX)) divided by the average of the STV during the screening window (STV (AVG)) is less than the set threshold. If not, then the potential apnea event detected (at 440) is determined to not be an apnea event at step 580. If so, then the method moves to step 550.

Steps 550 and 560 determine whether mixed rhythm types or outliers are present in the screening window to ensure that the potential apnea event detection was not triggered inappropriately due to morphology changes resulting from changes in cardiac rhythms, PVCs or other conditions, such as noise introduced by electronics or outside influences.

At step 550, a determination is made as to whether more than one type of cardiac rhythm is present within the screening window. For instance, if an atrial paced, ventricular paced rhythm is mixed with an atrial paced, ventricular sensed rhythm, or an atrial sensed, ventricular paced rhythm is mixed with an atrial sensed, ventricular sensed rhythm, the potential apnea event will be determined not to be an apnea event at step 580. If only one type of rhythm is present, then a determination is made at step 560 as to whether any peak-to-peak or area under the curve (AUC) outliers exist in the screening window.

In addition, single large amplitude PVCs or areas under the curve with fusion beats can lead to an incorrect apnea event prediction. At step 560, the relative difference between a current peak-to-peak or average under the curve value of the feature is calculated relative to immediate neighboring values. This may be performed calculating a pre- and post-difference value of the feature and comparing it to a threshold. The pre-difference value may be calculated by taking the value of a peak less the value of its preceding peak, dividing that sum by the value of the preceding peak, and taking the absolute value thereof. The post-difference value may be calculated by taking the value of a peak less the value of its succeeding peak, dividing that sum by the value of the succeeding peak, and taking the absolute value thereof. If pre- and post-difference values are greater than or equal to a threshold of, in one embodiment, 0.3, an outlier is determined to be present, and the potential apnea event is determined to not be an apnea event at step 580. For intrinsic R-waves, an additional evaluation at step 560 using an R-to-R interval criteria is used. If the pre- and post-difference values are greater than or equal to a second threshold, for example 0.15 in one embodiment, then a comparison of the timing of R-wave detections of three different R-waves is made to determine whether an outlier is present. This comparison may include comparing whether a difference between a first and second successive R-wave detection timing is less than eighty (80) percent of the second and a third successive R-wave detection timing. If so, then an outlier is determined.

At step 570, if apnea events are found in two measurement periods separated by less than a number of cardiac beats, for example, five cardiac beats, it is likely that the two apnea events are a single event. Thus, the events may be merged at step 570. At step 590, the apnea event is confirmed.

The Apnea—Hypopnea Index (AHI) is an index used to indicate the severity of sleep apnea. It is represented by the number of apnea and hypopnea events per hour of sleep. The total number confirmed apnea events may be divided by the total patient sleep time to provide a daily AHI estimate.

The aforementioned methods of FIGS. 3-5 may be performed in an IMD in real time as the device conducts other operations within a patient. In alternative embodiments, an IMD may obtain IEGM signal data and output that data to another processing system which performs the analysis described herein. Such other processing systems may be any suitable hardware, software, virtual or cloud-based processing system including code operable to instruct the processing system to perform the methods herein. In an IMD, the MCU may include code operable to instruct the MCU to perform the methods in real time, or upload results of the method for further analysis. Such results may include, without limitation, AHI, number and duration of apnea events, and timing of apnea events over a sleep period or multiple sleep periods.

Experimental results were obtained by applying the method discussed above to a data set of patients of who completed a sleep study using polysomnography (PSG) and each of whom had an implanted, dual chamber pacemaker. The method reported predictions of clinically moderate/ severe (AHI>15) and severe (AHI>30) events. In the results, sensitivity, specificity, positive predictive value (PPV) and negative predictive value (NPV) were obtained. The atrial and ventricular EGM from each patient's pacemaker was recorded while the patient performed a PSG over the course of a night of sleep. After acquisition, the PSG and EGM were time-synchronized for the purpose of analysis. Sensitivities for predicting AHI of greater than 15 and AHI of greater than 30 were 86% and 88% respectively using the present technology, with positive predictive values results showing similar results with 86% (12/14) and 78% (7/9). Specificity and NPV values are similar as well, as illustrated in table 1.

TABLE 1

|  | Sensitivity (%) | Specificity (%) | PPV (%) | NPV (%) |
|---|---|---|---|---|
| AHI > 15 | 86 | 87 | 86 | 87 |
| AHI > 30 | 88 | 90 | 78 | 95 |

Performance of the present technology was also evaluated by ventricular rhythm types (pacing vs. intrinsic). As shown in Table 2, the technology may perform better in ventricular pacing mode compared to ventricular sensed for both AHI cutoffs of 15 and 30 with a limited number of patients (N) for each type.

TABLE 2

|  | Ventricular Rhythm Type | Sensitivity (%) | Specificity (%) | PPV (%) | NPV (%) | Average Performance (%) |
|---|---|---|---|---|---|---|
| AHI > 15 | Sensed (N = 13) | 88 | 80 | 78 | 75 | 80 |
|  | Paced (N = 9) | 83 | 100 | 100 | 75 | 90 |
| AHI > 30 | Sensed (N = 13) | 75 | 80 | 75 | 80 | 78 |
|  | Paced (N = 9) | 100 | 89 | 80 | 100 | 92 |

Figure 6:
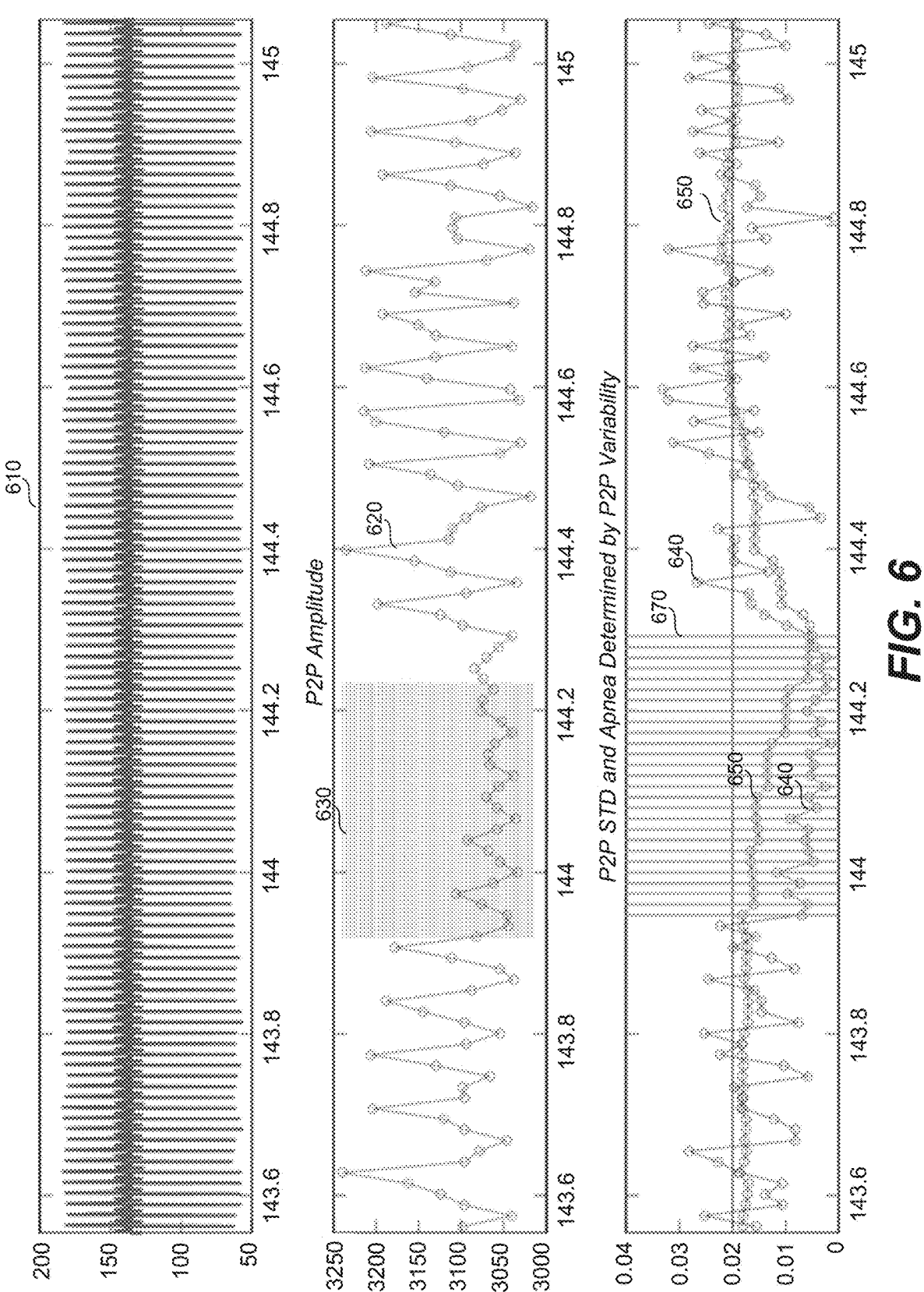
FIG. 6 shows an example of proper detection of one apnea/hypopnea event by the present technology.

FIG. 6 shows an example of proper detection of one apnea/hypopnea event by the present technology. FIG. 6 show is an example EGM segment 610 of approximately seventy (70) seconds. FIG. 6 also illustrates a plot 620 of the P2P amplitude for each cardiac cycle. Block 630 represents a human expert-adjudicated apnea/hypopnea event represented by the R-wave amplitude variability of the signal in the segment 630. In block 630, the P2P amplitudes were significantly reduced during the apnea event returning to normal amplitudes following the end of the apnea event. A plot 640 of the STV and a plot 650 of the LTV are shown, with block 670 representing the detected apnea event by the present technology. As shown in FIG. 6, the STV crosses LTV many times during normal breathing but became suppressed below the LTV in the block 670. The STV then crosses the LTV, marking the end of the apnea event.

As noted above, in certain embodiments, one of the methods for monitoring for apnea, as described above, is only performed when it is determined that a patient is sleeping, or at least likely to be sleeping. In other words, sleep apnea is monitored for when the patient is classified as being asleep, and is not monitored for when the patient is classified as being awake. During rest and sleep periods, the activity levels and rate of change in posture normally decreases in most patients. Certain embodiments of the present technology relate techniques for detecting sleep entry and exit using activity and/or posture data, as obtained from one or more sensors, such as, a three-dimensional (3D) accelerometer.

In accordance with certain embodiments, sleep entry is detected when a patient's activity level drops below a sleep threshold, and the patient's posture is either recumbent or reclined. In accordance with certain embodiments, sleep entry is detected when the patient's activity level increases above (i.e., exceeds) the sleep threshold, and the patient's posture is upright, where an upright posture includes any sitting or standing posture. The same component or subsystem that is used for detecting a patient's activity level can also be used to detect the patient's posture. It would also be possible for a first component or subsystem to be used for detecting the patient's activity level, and a second component or subsystem to be used for detecting the patient's posture. However, to minimize the number of components that are located within an IMD and that consume power from a battery of the IMD, it is beneficial to utilize the same component to both detect the patient's activity level and the patient's posture. Such a component can be a multi-dimensional accelerometer, such as a 3D accelerometer. A patient's posture is considered to be recumbent if they are lying on their back, stomach, left-side, or right-side. In other words, recumbent posture includes any of the lying down postures such as left-sided, right-sided, prone, and supine postures. A patient's posture is considered to be upright if the patient is standing or sitting generally upright. In other words, upright posture includes any of the sitting and standing postures where the patient's upper body is generally upright, as opposed to reclined or recumbent.

A 3D accelerometer includes sensors that generate first (X), second (Y) and third (Z) accelerometer signals along corresponding X, Y and Z axes (also referred to as first axis accelerometer signals, second axis accelerometer signals and third axis accelerometer signals). The X, Y and Z axes accelerometer signals collectively define a three-dimensional (3D), or multi-dimensional (MD), accelerometer data set. While examples herein are described in connection with an accelerometer that generates accelerometer signals along three orthogonal axes, it is recognized that embodiments may be implemented wherein accelerometer signals are generated along two or more axes, including more than three axes. A 3D accelerometer can include one or more analog-to-digital converters (ADCs) that convert analog X, Y, and Z axes accelerometer signals to digital signals, based upon which an activity level and a posture can be determined. One example of such a 3D accelerometer is described in U.S. Pat. No. 6,937,900, titled "AC/DC Multi-Axis Accelerometer for Determining A Patient Activity And Body Position," the complete subject matter which is expressly incorporated herein by reference.

Figure 7A:
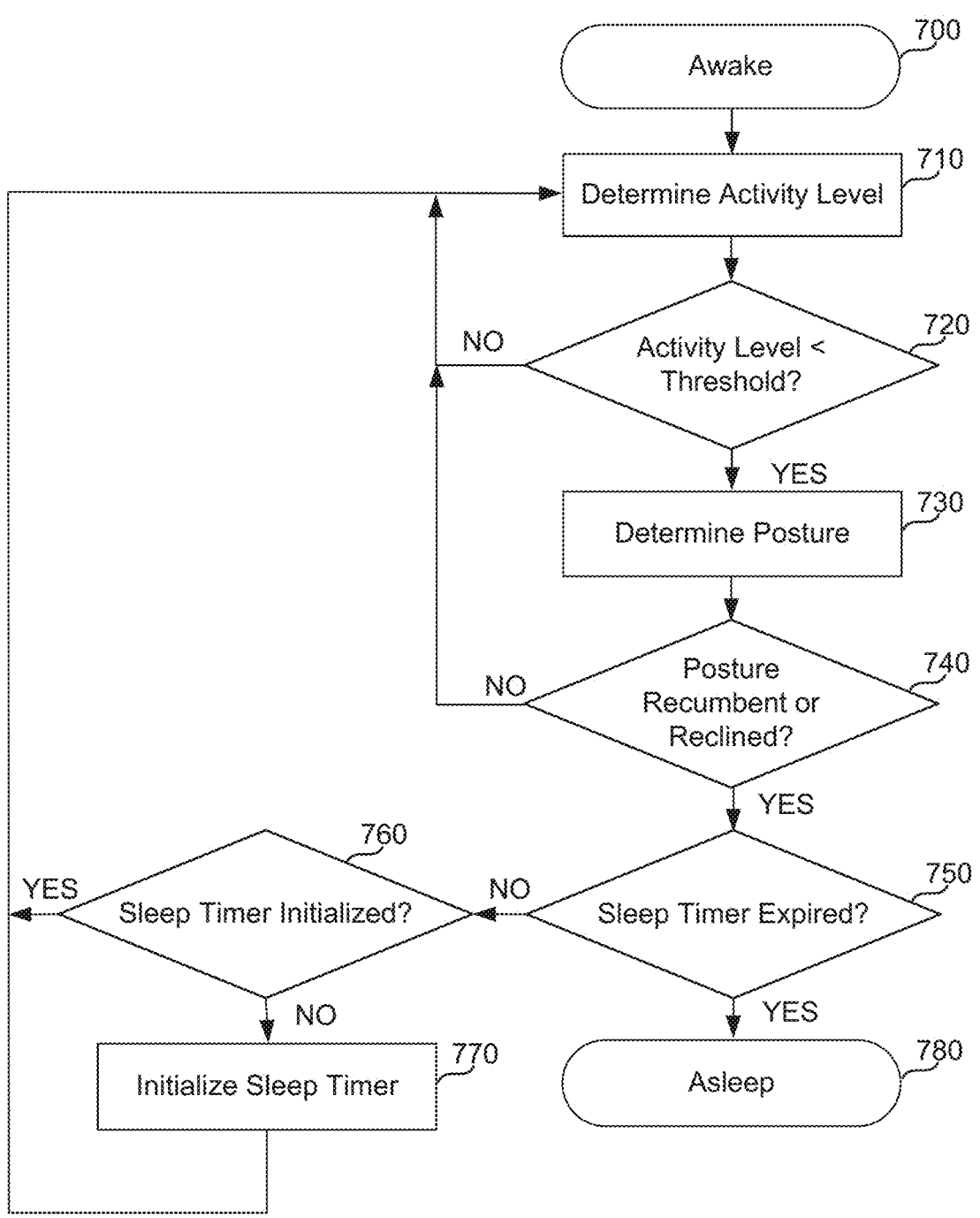
FIG. 7A illustrates a method for detecting sleep entry, in accordance with an embodiment of the present technology.
Figure 8A:
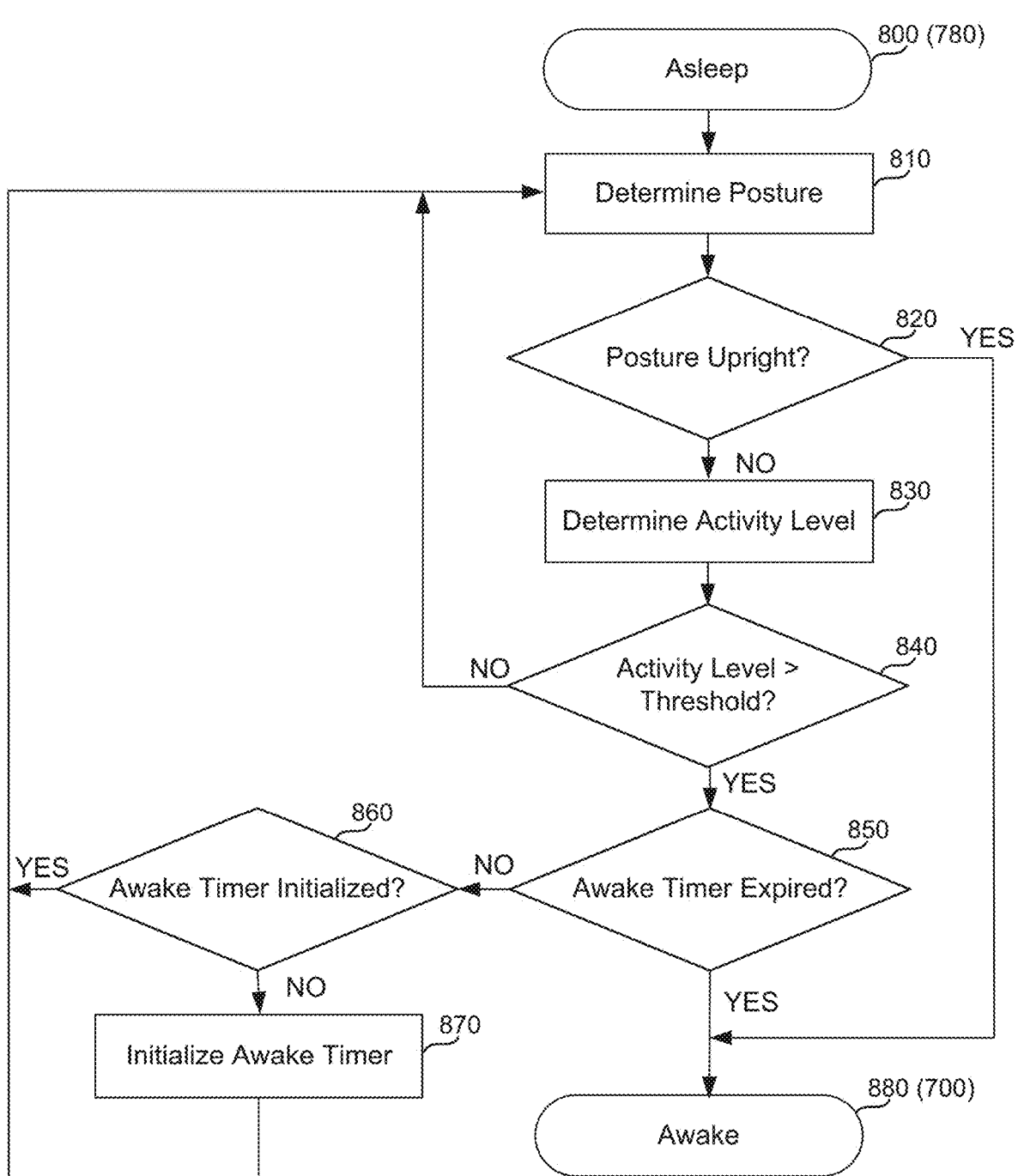
FIG. 8A illustrates a method for detecting sleep exit, in accordance with an embodiment of the present technology.
Figure 9:
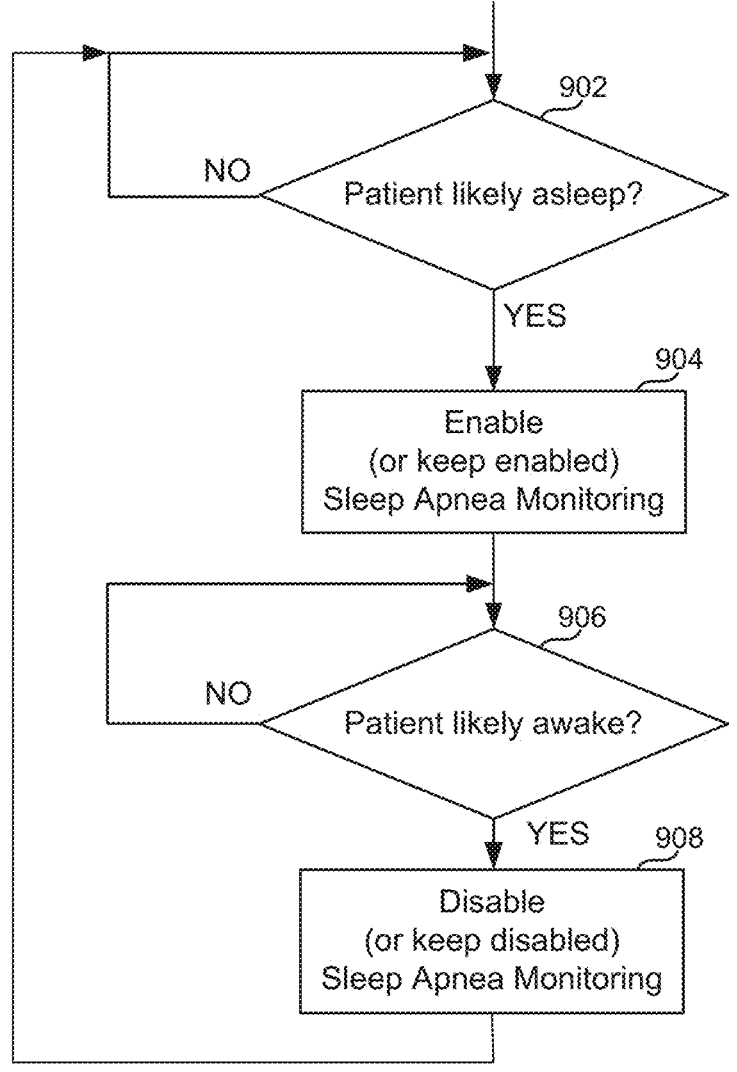
FIG. 9 illustrates how an embodiment that is used to monitor for a potential sleep apnea event can be enabled in response to sleep entry being detected, and can be disabled in response to sleep exit being detected, in accordance with specific embodiments of the present technology.

The high level flow diagram of FIG. 7A is used to explain how a 3D accelerometer can be used to detect sleep entry, in accordance with certain embodiments of the present tech-nology. Thereafter, the high level flow diagram of FIG. 8A is used to explain how the same 3D accelerometer can be used to detect sleep exit. The term sleep entry, as used herein, refers to a patient's transition from a non-sleep state to a sleep state. The term sleep exit, as used herein, refers to a patient's transition from a sleep state to a non-sleep state. FIG. 9 will then be used to explain how an embodiment that is used to monitor for a potential sleep apnea event can be enabled in response to sleep entry being detected, and can be disabled in response to sleep exit being detected, in accor-dance with specific embodiments of the present technology. Such embodiments are useful for improving the autonomous monitoring for sleep apnea, because a patient cannot experience sleep apnea when they are awake, i.e., when they are in a non-sleep state. Accordingly, such embodiments can be used to reduce the number of potential false positive detections of potential sleep apnea events.

Referring to FIG. 7A, the method summarized therein begins while the patient is awake (i.e., in a non-sleep state), as indicated by block 700. At step 710 there is a determi-nation of the activity level of the patient, which can be performed by reading the z-axis data from a 3D accelerom-eter, but is not limited thereto. At step 720 there is a determination of whether the activity level is less than a specified threshold, which can be referred to as the sleep threshold. If the answer to the determination at step 720 is NO, then flow returns to step 710. If the answer to the determination at step 720 is YES, then flow goes to step 730.

At step 730 there is a determination of the patient's posture, which can be performed by reading data from multiple axis of the 3D accelerometer (e.g., two of the x-, y-, and z-axis), and preferably, three axis of the 3D accelerom-eter (e.g., all three of the x-, y-, and z-axis). At step 740 there is a determination of whether the patient's posture is recum-bent or reclined, which are the most likely postures a patient will have when asleep. If the answer to the determination at step 740 is NO, then flow returns to step 710. If the answer to the determination at step 740 is YES, then flow goes to step 750.

At step 750 there is a determination of whether a sleep timer (e.g., 134 in FIG. 1) has expired. The sleep timer, aka the S_TIMER, can be configured to count-up, or count-down, for a specified amount of time (e.g., 10 minutes) once initiated, at which point the sleep timer expires. The speci-fied amount of time, which can also be referred to as the sleep latency duration, is how long it is expected for a patient to fall asleep after initially lying down to try to go to sleep. In accordance with certain embodiments, the specified amount of time can be 10 minutes. However, the use of shorter or longer sleep latency durations are also possible and within the scope of the embodiments disclosed herein. If the answer to the determination at step 750 is NO, the flow goes to step 760.

At step 760 there is a determination of whether the sleep timer has been initialized. If the answer to the determination at step 760 is YES, then flow returns to step 710. If the answer to the determination at step 760 is NO, then flow goes to step 770, at which step the sleep timer is initialized. Initialization of the sleep timer can involve starting the sleep timer, or resetting and then starting the sleep timer. After step 770, flow returns to step 710.

Returning to step 750, if the answer to the determination at step 750 is YES, then it is determined that the patient is asleep, as indicated by block 780. More generally, in the embodiment summarized with reference to FIG. 7A, a patient will be determined to be asleep (i.e., be classified as being asleep), in response to the patient both having an activity level below a specified threshold level and the patient's posture being either recumbent or reclined, for at least the threshold amount of time (aka the sleep latency duration).

FIG. 7B shows example pseudocode that can be used to implement the method summarized with reference to the flow diagram of FIG. 7A. As can be appreciated from FIG. 7B, a patient can be classified as being asleep if both of the following conditions are satisfied for at least the specified amount of time (aka the sleep latency duration), e.g., 10 minutes: (a) the patient's posture is either recumbent or reclined, and (b) patient's activity level is below the specified activity threshold. The activity threshold can also be referred to herein as the activity level threshold.

Reference is now made to the high level flow diagram of FIG. 8A, which as noted above, is used to explain how the 3D accelerometer can be used to detect sleep exit, which is a transition from a sleep state to a non-sleep state. Referring to FIG. 8A, at step 810 there is a determination of the patient's posture, which can be performed by reading data from multiple axis of the 3D accelerometer, and preferably, three axis of the 3D accelerometer. At step 820 there is a determination of whether the posture is upright, which is the most likely posture a patient will have when awake. If the answer to the determination at step 820 is NO, then flow goes to step 830. If the answer to the determination at step 820 is YES, then flow goes to step 880, at which block it is determined that the patient is awake (i.e., classified as being awake). This is because if a patient has transitioned from having a recumbent or reclined posture, while asleep, to having an upright posture, the patient has most likely awoken.

If the answer to the determination at step 820 is NO, the flow goes to step 830. At step 830 there is a determination of the activity level of the patient, which can be performed by reading the z-axis data from a 3D accelerometer, but is not limited thereto. At step 840 there is a determination of whether the activity level is greater than a specified threshold, which can be referred to as the awake threshold. The awake threshold used at step 840 can be the same as the sleep threshold used at 720, however, that need not be the case.

If the answer to the determination at step 840 is NO, then flow returns to step 810. If the answer to the determination at step 840 is YES, then flow goes to step 850.

At step 850 there is a determination of whether an awake timer (e.g., 136 in FIG. 1) has expired. The awake timer, aka the W_TIMER, can be configured to count-up, or count-down, for a specified amount of time (e.g., 2 minutes) once initiated, at which point the awake timer expires. The specified amount of time, which can also be referred to as the awake latency duration, is amount of time after which it is presumed a patient has woken up if the patient's activity level remains above the specified threshold level for that amount of time. In accordance with certain embodiments, the specified amount of time can be 2 minutes. However, the use of shorter or longer awake latency durations, and thus shorter or longer awake thresholds, are also possible and within the scope of the embodiments disclosed herein. If the answer to the determination at step 850 is NO, the flow goes to step 860.

At step 860 there is a determination of whether the awake timer has been initialized. If the answer to the determination at step 860 is YES, then flow returns to step 810. If the answer to the determination at step 860 is NO, then flow goes to step 870, at which step the awake timer is initialized. Initialization of the awake timer can involve starting the awake timer, or resetting and then starting the awake timer. After step 870, flow returns to step 810.

Returning to step 850, if the answer to the determination at step 850 is YES, then it is determined that the patient is awake, as indicated by block 880. More generally, in the embodiment summarized with reference to FIG. 8A, a patient will be determined to have be awake, in response to the patient either having an upright posture, or having an activity level above a specified threshold level, for at least the threshold amount of time (aka the awake latency duration).

FIG. 8B shows example pseudocode that can be used to implement the method summarized with reference to the flow diagram of FIG. 8A. As can be appreciated from FIG. 8B, a patient can be classified as being awake if one of the following conditions are satisfied for at least the specified amount of time (aka the awake latency duration), e.g., 2 minutes: (a) the patient's posture is upright, or (b) patient's activity level is above the specified activity threshold.

FIG. 9 will now be used to explain how an embodiment that is used to monitor for a potential sleep apnea event can be enabled in response to sleep entry being detected, and can be disabled in response to sleep exit being detected, in accordance with specific embodiments of the present technology. Such embodiments are useful for improving the autonomous monitoring for sleep apnea, because a patient cannot experience sleep apnea when they are awake, i.e., when they are in a non-sleep state. Accordingly, such embodiments can be used to reduce the number of potential false positive detections of potential sleep apnea events. The patient is likely to be asleep when they are classified as being asleep.

Referring to FIG. 9, at step 902 there is a determination of whether a patient is likely asleep. Such a determination can be made, for example, using the embodiment described above with reference to FIG. 7A. In such an embodiment, an accelerometer is used to obtain posture information and activity information, and the detection of when the patient is likely sleeping is based on the posture information and the activity information. If the answer to the determination at step 902 is NO, then flow returns to step 902. If the answer to the determination at step 902 is YES, then flow goes to step 904.

At step 904 sleep apnea monitoring is enabled, or if already enabled, continues to be enabled. Such sleep apnea monitoring can include determining a measure of STV and a measure of LTV of a feature of the signal indicative of cardiac electrical activity of a patient's heart over a measurement period that includes a plurality of cardiac cycles, wherein the feature comprises one of a morphological feature or a temporal feature, and monitoring for a potential apnea event in the measurement period based on the measure of STV and the measure of LTV in the feature. In other words, in response to detecting that the patient is likely sleeping, there can be an enabling of the determining of the measure of STV and the measure of LTV that are used for detecting the potential apnea event. Additional details of how a measure of STV and a measure of LTV can be used for detecting a potential apnea event are described above with reference to FIGS. 2-6.

Still referring to FIG. 9, at step 906 there is a determination of whether a patient is likely awake. Such a determination can be made, for example, using the embodiment described above with reference to FIG. 8A. In such an embodiment, an accelerometer is used to obtain posture information and/or activity information, and the detection of when the patient is likely awake is based on the posture information, and/or based on the activity information. If the answer to the determination at step 906 is NO, then flow returns to step 906. If the answer to the determination at step 906 is YES, then flow goes to step 908. At step 908 sleep apnea monitoring is disabled, or if already disabled, continues to be disabled. Flow then returns to step 902. The patient is likely to be awake when the patient is classified as being awake.

Figure 10:
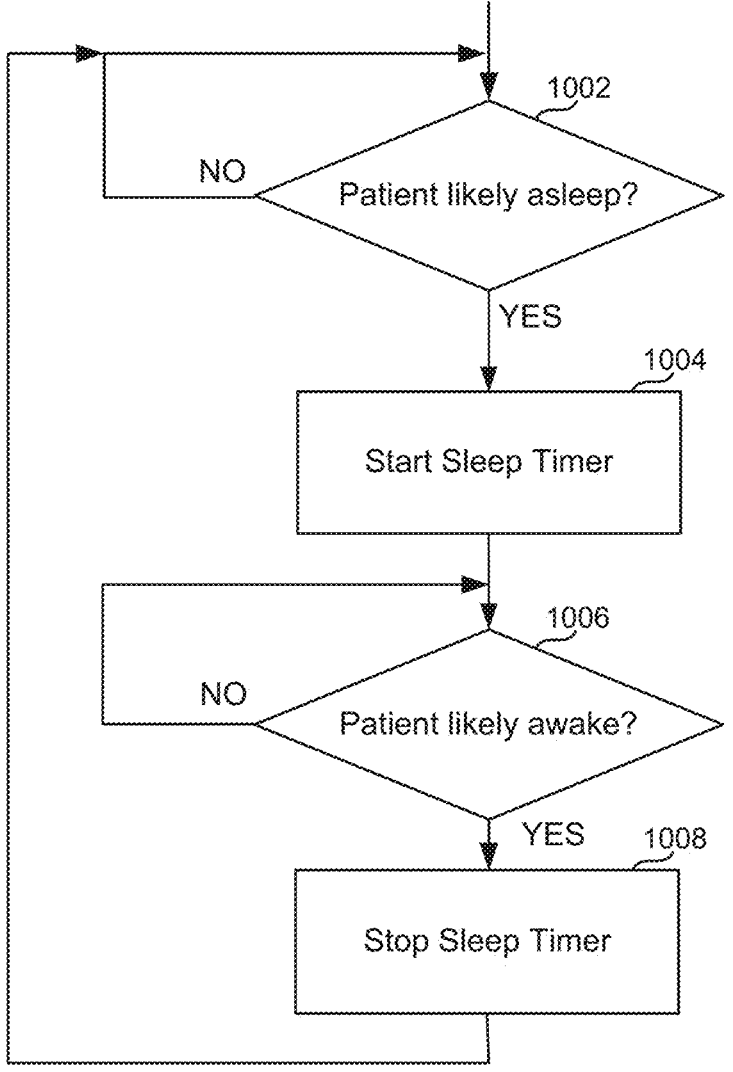
FIG. 10 illustrates how the sleep entry and sleep exit techniques, described with reference to FIGS. 6 and 7, can be used to monitor the amount of sleep a patient gets continuously and/or within a specified period of time.

The amount of sleep patients get plays a vital role in the quality of life for patients. Precise and accurate methods for detecting sleep entry and exit are important to calculate total sleep period. FIG. 10 will now be used to explain how the sleep entry and sleep exit techniques, described above with reference to FIGS. 6 and 7, can be used to monitor the amount of sleep a patient gets continuously and/or within a 24 hour period, or some other specified period.

Referring to FIG. 10, at step 1002 there is a determination of whether a patient is likely asleep. Such a determination can be made, for example, using the embodiment described above with reference to FIG. 7A. In such an embodiment, an accelerometer is used to obtain posture information and activity information, and the detection of when the patient is likely sleeping is based on the posture information and the activity information. If the answer to the determination at step 1002 is NO, then flow returns to step 1002. If the answer to the determination at step 1002 is YES, then flow goes to step 1004. At step 1004 a sleep timer (e.g., 134 in FIG. 1, or a separate sleep timer) is started.

Still referring to FIG. 10, at step 1006 there is a determination of whether a patient is likely awake. Such a determination can be made, for example, using the embodiment described above with reference to FIG. 8A. In such an embodiment, an accelerometer is used to obtain posture information and/or activity information, and the detection of when the patient is likely awake is based on the posture information, and/or based on the activity information. If the answer to the determination at step 1006 is NO, then flow returns to step 1006. If the answer to the determination at step 1006 is YES, then flow goes to step 1008. At step 1008 the sleep timer is stopped.

In certain embodiments, each time the sleep timer is stopped, a value of the sleep timer is stored in memory (e.g., 120) along with a time stamp or the like, which saved value can specified how long a patient continuously slept. This assumes the sleep timer is reset each time the patient transitions from being asleep to being awake, or from being awake to being asleep. In an alternative embodiment, the sleep timer can be rest once per day, e.g., at 11:00 a.m. each day, and the sleep timer can be used keep track of a total amount of sleep that a patient gets during each day (i.e., during each 24 hour period) or during some other specified period of time (e.g., a 7 day period, aka a week), and such information can be stored in memory (e.g., 120).

Referring briefly back to the flow diagrams of FIGS. 7A and 8A, at step 720 in FIG. 7A and step 840 in FIG. 8A, a patient's activity level is compared to a threshold, which can be referred to as an activity threshold. The activity threshold can be a predetermined value, or alternatively, can be a dynamic value that is updated from time to time based on measurements of activity obtained from an accelerometer (e.g., 125 in FIG. 1). Various ways of producing a dynamic activity threshold, according to various embodiments of the present technology, are described below.

In certain embodiments, described below with reference to FIGS. 11A and 11B, a histogram is generated using activity data (e.g., z-axis activity data) obtained using an accelerometer over a specified period of time (e.g., a 7 day period, aka a week). As an example, activity data can be obtained once per second and used to generate a histogram. An activity threshold can then be determined as being equal to the activity level value below which there is a specified percent (e.g., 33 percent) of the activity counts included in the histogram. In alternative embodiments, an activity threshold, for use in the sleep entry and sleep exit detection techniques described above, is set as being equal to a long term average (LTA) or a long term moving average (LTMA) of activity data (e.g., z-activity data) obtained using an accelerometer over a specified period of time (e.g., a 7 day period, aka a week). The activity threshold can be defined as being equal to the LTA or the LTMA. Alternatively, the activity threshold can be defined as being equal to the LTA or the LTMA plus a specified offset.

In each of the embodiments described above, which involve comparing a detected activity level to an activity threshold, the activity level and the activity threshold can be for a single axis of activity data, such as z-axis activity data. Alternatively, activity level data can be obtained for multiple axis, e.g., two or three axis, and more specifically two of the x-, y-, and z-axes, or all three of the x-, y-, and z-axes. Where activity level data is obtained and analyzed for multiple axes, the activity level data for the multiple axes can be combined (e.g., added or averaged) and then compared to an appropriate activity threshold. Alternatively, for each separate axis, obtained activity level data can be separately compared to a respective activity threshold. For example, where activity level data for each of the three separate axis is compared to a respective activity threshold (i.e., an x-axis threshold, a y-axis threshold, and a z-axis threshold), the patient's activity level can be determined to exceed the threshold(s), such that the answer to the determination at step 720 or step 840 is Yes, if one of the three thresholds is exceeded, if two of the three thresholds are exceeded, or if all three of the thresholds are exceeded, depending upon the specific implementation. It would also be possible to utilized activity data for just two of the above mentioned three axes, rather than for all three axes. Data from two axes can be combined (e.g., added or averaged) and then compared to an appropriate threshold, or data from each of the two axes can be compared to a respective threshold. Where activity level data for each of the two separate axis is compared to a respective activity threshold (i.e., an x-axis threshold and a z-axis threshold), the patient's activity level can be determined to exceed the threshold(s), such that the answer to the determination at step 720 or step 840 is Yes, if one of the two thresholds is exceeded, or if both of the two thresholds are exceeded, depending upon the specific implementation.

Figures 11A, 11B:
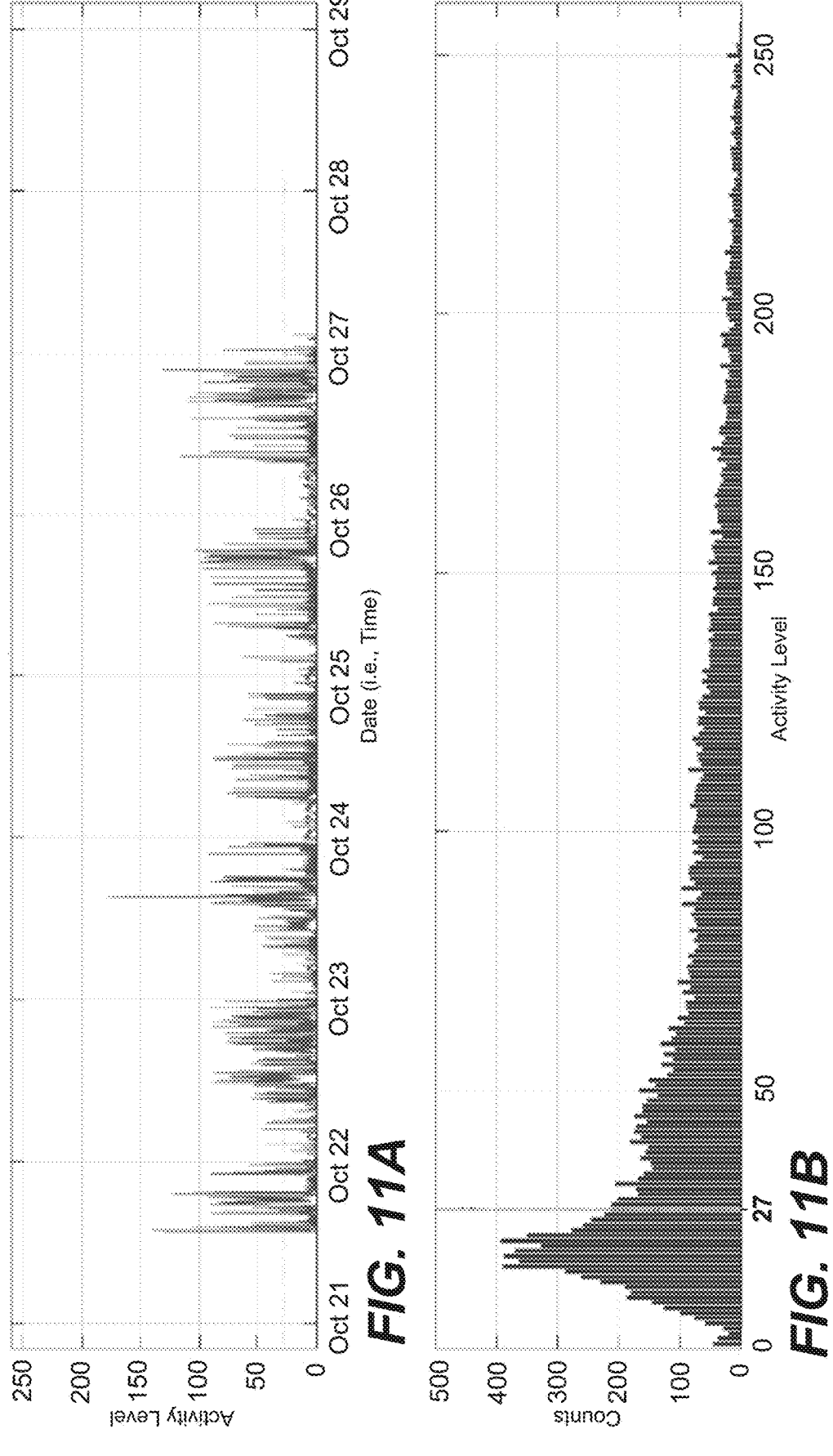
FIG. 11A is an example graph showing activity data collected over a number of days.
FIG. 11B illustrates an example of a histogram that can be used to determine an activity threshold, for use in the sleep entry and sleep exit detection techniques, in accordance with certain embodiments of the present technology, wherein the histogram is produced using the activity data shown in FIG. 11A.

FIG. 11A is an example graph showing activity data (e.g., z-axis activity data) collected over a number of days, which includes October 22, October 23, October 24, October 25, October 26, and October 27. In FIG. 11A, the days are indicated along the horizontal axis, and activity levels are indicated along the vertical axis. FIG. 11B illustrates an example of a histogram produced using the activity data shown in FIG. 11A. In FIG. 11B, activity level bins are indicated along the horizontal axis, and the activity counts within each of the bins is specified along the vertical axis. In accordance with an embodiment, an activity threshold is determined by summing up all of the activity counts included in the histogram, and setting the activity threshold as being equal to a specified percent (e.g., 33 percent) of the total activity counts. In the example of FIG. 11B, the activity level at 33 percent of the total activity counts is 27, meaning in the Example of FIG. 11B the activity threshold is set to an activity level of 27.

Figure 12:
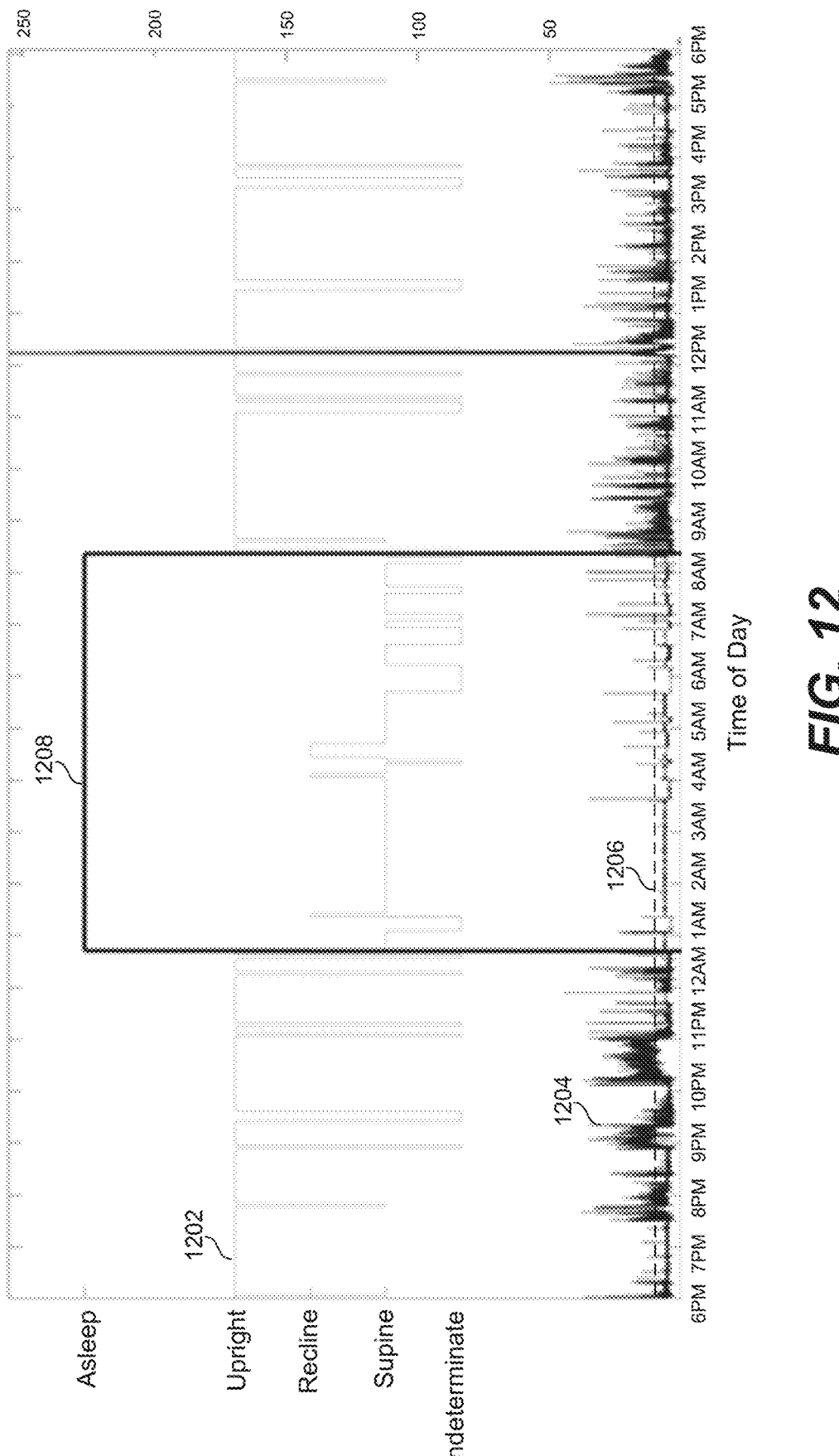
FIG. 12 illustrates exemplary results of using an embodiment of the present technology to classify when a patient is awake and when the patient is asleep.

FIG. 12 includes a graph that illustrates how certain embodiments of the present technology described above can be used to detect when a patient is asleep over a 24 hour period, between 6 PM of one day and 6 PM of the following day. In FIG. 12, the line labeled 1202 indicates the posture of the patient as determined from accelerometer data or detected by the accelerometer, the line labeled 1204 indicates the activity level along the z-axis as detected by the accelerometer, the dashed line labeled 1206 indicates the activity threshold, and the line labeled 1208 indicates when the patient is asleep. In this example, the activity threshold is set to an activity level of 10, the patent is classified as being asleep when both of the following conditions are satisfied for at least the sleep latency duration of 10 minutes: (a) the patient's posture is either recumbent or reclined, and (b) patient's activity level is below the specified activity threshold. Additionally, in this example the patient is classified as being awake (aka not asleep) when one of the following conditions is satisfied for at least the awake latency duration of 2 minutes: (a) the patient's posture is upright, or (b) patient's activity level is above the specified activity threshold.

As can be appreciated from FIG. 12, the patient was classified as being asleep from 12:30 AM to 8:30 AM, and thus, was asleep for about 8 hours consecutively, and 8 hours total within the 24 hour period. During the other periods of time the patient was classified as being awake. The phrases classified as being awake and determined to be awake, and similar phrases, as used herein, are used interchangeable. Similarly, the phrases classified as being asleep and determined to be asleep, and similar phrases, as used herein, are used interchangeably. Where an IMD is configured to only monitor for apnea while a patient is classified as being asleep, in the example of FIG. 12, apnea events are only monitored for between 12:30 AM and 8:30 AM. Additionally, or alternatively, other methods (besides apnea detection methods) can be enabled while a patient is classified as being asleep, and can be disabled while a patient is classified as being awake, or vise-versa. For an example, a method for monitoring of sleep quality may be enabled while a patient is classified as being asleep, and may be disabled while a patient is classified as being awake. Such a method can, for example, monitor a patient's hear rate variability (HRV) wherein the patient is asleep and can utilize a measure of HRV to determine the patient's sleep quality, while higher measures of HRV is indicative of good sleep quality, and lower measures of HRV is indicative of poor sleep quality. A numeric sleep score ban be produced, saved, and/or output. Additionally, or alternatively, a sleep quality indicator can be produced, saved, and/or output, examples of which include poor, good, and excellent. Other variations are also possible and within the scope of the embodiments described herein.

An algorithm or technique that is used to classify a patient as being asleep or awake, as disclosed herein, can be used to determine when to enable and disable certain other algorithms or techniques, such as the determining of the measure of STV and the measure of LTV that are used for detecting a potential apnea event, as was described above. An algorithm or technique that is used to classify a patient as being asleep or awake, as disclosed herein, can alternatively be used completely independently of the algorithms or techniques described herein that are use for detecting a potential apnea event, e.g., to selectively enable and disable other algorithms or techniques, and/or to monitor how long a patient continually sleeps and/or collectively sleeps over a specified period of time. Other variations are also possible and within the scope of the embodiments described herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

Embodiments of the present technology have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. 3-5 and 7A-10.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

27

28

What is claimed is:

1. An apparatus, comprising:

an accelerometer; and a processor;

the accelerometer, alone or in combination with the processor, used to determine an activity level of a patient and a posture of the patient;

the processor configured to classify the patient as being asleep in response to both (i) the posture of the patient being recumbent or reclined for at least a sleep latency duration, and (ii) the activity level of the patient not exceeding an activity threshold for at least the sleep latency duration;

after the patient has been classified as being asleep, classify the patient as being awake in response to at least one of (iii) the posture of the patient being upright for at least an awake latency duration, or (iv) the activity level of the patient exceeding the activity threshold for at least the awake latency duration; enable monitoring for apnea or monitoring of the patient's sleep quality, or both, in response to the patient being classified as being asleep; and disable monitoring for apnea or monitoring of the patient's sleep quality, or both, in response to the patient being classified as being awake.

2. The apparatus of claim 1, wherein the sleep latency duration is longer than the awake latency duration.

3. The apparatus of claim 1, wherein the apparatus comprises an implantable medical device.

4. The apparatus of claim 3, wherein the implantable medical device is configured to selectively deliver therapy to a patient within which the implantable medical device is implanted.

5. The apparatus of claim 4, wherein the processor is configured to adjust at least one parameter used to deliver the therapy based on whether the patient is classified as being asleep or awake.

6. The apparatus of claim 1, wherein the processor is configured to adjust at least one parameter used to detect an arrythmia based on whether the patient is classified as being asleep or awake.

7. The apparatus of claim 1, wherein the processor is further configured to:

detect the activity level of the patient over a period of time;

produce a histogram based on the activity level of the patient over the period of time, the histogram including a plurality of bins each of which is associated with a different activity level and includes a respective number of activity counts; and determine the activity threshold based on the histogram.

8. The apparatus of claim 7, wherein the processor is configured to:

determine a total number of activity counts included in the histogram;

determine the activity level corresponding to a specified percent of the total number of activity counts; and determine the activity threshold as being equal to the activity level corresponding to the specified percent of the total number of activity counts.

9. The apparatus of claim 1, wherein the processor is configured to:

determine one of a long term average (LTA) or a long term moving average (LTMA) of the activity level of the patient over a period of time; and determine the activity threshold as being equal to the one of the LTA or the LTMA of the activity level of the patient, or as being equal to the one of the LTA or the LTMA of the activity level of the patient plus a specified offset;

wherein the one of the LTA or the LTMA changes over time, and thus, the activity threshold determined by the processor also changes over time.

10. The apparatus of claim 1, wherein the processor is configured to:

enable the monitoring of the patient's sleep quality in response to the patient being classified as being asleep; and disable the monitoring of the patient's sleep quality in response to the patient being classified as being awake.

11. The apparatus of claim 10, wherein:

the apparatus includes or is communicatively coupled to electrodes that are used to sense a signal indicative of electrical activity of the patient's heart; and the processor, in order monitor the patient's sleep quality while the patient is classified as being asleep, is configured to:

determine the patient's heart rate variability (HRV) based on the signal indicative of electrical activity of the patient's heart that is sensed while the patient is classified as being asleep;

determine the patient's sleep quality based on the patient's HRV; and save information indicative of the patient's sleep quality in a memory of, or communicatively coupled to, the apparatus.

12. The apparatus of claim 1, wherein the processor is configured to:

enable the monitoring for apnea in response to the patient being classified as being asleep; and disable the monitoring for apnea in response to the patient being classified as being awake.

13. The apparatus of claim 1, wherein the processor is further configured to monitor an amount of sleep the patient gets continuously, monitor an amount of sleep the patient gets within a specified period, or both.

14. A method for use by an apparatus including an accelerometer and a processor, the method comprising:

determining an activity level of a patient using the accelerometer;

determining a posture of the patient using the accelerometer;

the processor, during a first period of time, classifying the patient as being asleep in response to both (i) the posture of the patient being recumbent or reclined for at least a sleep latency duration, and (ii) the activity level of the patient not exceeding an activity threshold for at least the sleep latency duration; and enabling monitoring for apnea or monitoring of the patient's sleep quality, or both, in response to the patient being classified as being asleep;

the processor, during a second period of time, after the patient has been classified as being asleep during the first period of time, classifying the patient as being awake in response to at least one of (iii) the posture of the patient being upright for at least an awake latency duration, or (iv) the activity level of the patient exceeding the activity threshold for at least the awake latency duration; and disabling monitoring for apnea or monitoring of the patient's sleep quality, or both, in response to the patient being classified as being awake.

15. The method of claim 14, wherein the sleep latency duration is longer than the awake latency duration.

16. The method of claim 14, wherein the apparatus comprises an implantable medical device that includes the accelerometer and the processor.

17. The method of claim 16, further comprising the implantable medical device selectively delivering therapy to the patient within which the implantable medical device is implanted.

18. The method of claim 17, further comprising the processor adjusting at least one parameter used to deliver the therapy based on whether the patient is classified as being asleep or awake.

19. The method of claim 14, further comprising the processor adjusting at least one parameter used to detect an arrythmia based on whether the patient is classified as being asleep or awake.

20. The method of claim 14, further comprising:
detecting the activity level of the patient over a period of time using the accelerometer;
producing a histogram based on the activity level of the patient over the period of time, the histogram including a plurality of bins each of which is associated with a different activity level and includes a respective number of activity counts; and
determining the activity threshold based on the histogram.

21. The method of claim 20, wherein the determining the activity threshold based on the histogram comprises:
determining a total number of activity counts included in the histogram;
determining the activity level corresponding to a specified percent of the total number of activity counts; and
determining the activity threshold as being equal to the activity level corresponding to the specified percent of the total number of activity counts.

22. The method of claim 14, further comprising:
determining one of a long term average (LTA) or a long term moving average (LTMA) of the activity level of the patient over a period of time; and
determining the activity threshold as being equal to the one of the LTA or the LTMA of the activity level of the patient, or as being equal to the one of the LTA or the LTMA of the activity level of the patient plus a specified offset;
wherein the one of the LTA or the LTMA changes over time, and thus, the activity threshold also changes over time.

23. The method of claim 14,
wherein the disabling comprises disabling the monitoring of the patient's sleep quality in response to the patient being classified as being awake;
further comprising enabling the monitoring of the patient's sleep quality in response to the patient being classified as being asleep.

24. The method of claim 23, further comprising:
using electrodes of, or communicatively coupled to, the apparatus to sense a signal indicative of electrical activity of the patient's heart;
determining the patient's heart rate variability (HRV) based on the signal indicative of electrical activity of the patient's heart that is sensed while the patient is classified as being asleep;
determining the patient's sleep quality based on the patient's HRV; and
saving information indicative of the patient's sleep quality in a memory of, or communicatively coupled to, the apparatus.

25. The apparatus of claim 1, comprising a sleep timer implemented by the processor or external to the processor, wherein the processor is configured to:
initialize and start the sleep timer in response to determining that both the activity level of the patient does not exceed the activity threshold and the posture of the patient is recumbent or reclined;
reset the sleep timer, once started, in response to determining that the activity level of the patient exceeds the activity threshold or the posture of the patient is no longer recumbent or reclined, and
classify the patient as being asleep in response to the sleep timer counting-up or counting-down without being reset for a specified amount of time corresponding to the sleep latency duration.

26. The apparatus of claim 25, comprising an awake timer implemented by the processor or external to the processor, wherein the processor is configured to:
after and while the patient is classified as being asleep, initialize and start the awake timer in response to determining that the activity level of the patient exceeds the activity threshold;
reset the awake timer, once started, in response to determining that the activity level of the patient does not exceed the activity threshold; and
classify the patient as being awake in response to the awake timer counting-up or counting-down without being reset for a further specified amount of time corresponding to the awake latency duration.

27. The method of claim 14, wherein the disabling comprises disabling the monitoring of apnea in response to the patient being classified as being awake; and
further comprising enabling the monitoring for apnea in response to the patient being classified as being asleep.

28. The method of claim 14, further comprising monitoring an amount of sleep the patient gets continuously, monitoring an amount of sleep the patient gets within a specified period, or both.

* * * * *